US012758155B2

(12) United States Patent
An et al.

(10) Patent No.: US 12,758,155 B2

(45) Date of Patent: Oct. 13, 2026

(54) DISPLAY DEVICE INCLUDING A FORCE SENSOR, A LIGHT RECEIVING SENSOR, AND A MAIN PROCESSOR

(71) Applicant: SAMSUNG DISPLAY CO., LTD., Yongin-si (KR)

(72) Inventors: Jong Yeop An, Hwaseong-si (KR); Gyeong Ub Moon, Suwon-si (KR); Bo Ram Choi, Asan-si (KR); Hyeon Jun Lee, Hanam-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 147 days.

(21) Appl. No.: 17/816,640

(22) Filed: Aug. 1, 2022

(65) Prior Publication Data

US 2023/0172553 A1 Jun. 8, 2023

(30) Foreign Application Priority Data

Dec. 2, 2021 (KR) ........................ 10-2021-0170958

(51) Int. Cl.

*A61B 5/00* (2006.01)
*A61B 5/021* (2006.01)
(Continued)

(52) U.S. Cl.

CPC ........ *A61B 5/6898* (2013.01); *A61B 5/02116* (2013.01); *A61B 5/02125* (2013.01); *G01L 1/22* (2013.01); *A61B 5/02427* (2013.01)

(58) Field of Classification Search

CPC .............. A61B 5/6898; A61B 5/02116; A61B 5/02125; A61B 5/02427; A61B 5/0261;
(Continued)

(56) References Cited

U.S. PATENT DOCUMENTS

| | | | | |
|---|---|---|---|---|
| 4,263,918 | A * | 4/1981 | Swearingen | ....... A61B 5/02116 600/494 |
| 9,049,998 | B2 | 6/2015 | Brumback et al. | |

(Continued)

FOREIGN PATENT DOCUMENTS

| | | |
|---|---|---|
| KR | 10-2017-0049280 | 5/2017 |
| KR | 10-2017-0091047 | 8/2017 |

(Continued)

OTHER PUBLICATIONS

Papaioannou, T. et al. May 2016, Mean arterial pressure values calculated using seven different methods and their associations with target organ deterioration in a single-center study of 1878 individuals. Hypertension Research (2016) 39, 640-647 (Year: 2016).*

(Continued)

*Primary Examiner* — Anh Tuan T Nguyen
*Assistant Examiner* — Dean N Edun
(74) *Attorney, Agent, or Firm* — F. CHAU & ASSOCIATES, LLC

(57) ABSTRACT

A display device capable of measuring a user's blood pressure by analyzing a photoplethysmographic signal is disclosed. The display device includes a display panel including a plurality of pixels; a force sensor disposed on a surface of the display panel, the force sensor configured to sense an external force; a light receiving sensor disposed between a group of neighboring pixels of the plurality of pixels, or disposed in a through hole in a front portion of the display panel, the light receiving sensor configured to sense an amount of light reflected toward the display panel and generate an optical signal corresponding to the amount of light; and a main processor configured to generate a pulse wave signal according to the optical signal received from the light receiving sensor and analyze a magnitude, a period, and a wave change of the pulse wave signal.

23 Claims, 30 Drawing Sheets

(51) Int. Cl.
*A61B 5/024* (2006.01)
*G01L 1/22* (2006.01)

(58) Field of Classification Search
CPC ....... A61B 5/02416; A61B 5/02; A61B 5/021; A61B 5/02108; A61B 5/6843; A61B 5/02141; A61B 5/742; G01L 1/22; G06F 1/1601; H10K 59/60
See application file for complete search history.

(56) References Cited

U.S. PATENT DOCUMENTS

| | | | | |
|---|---|---|---|---|
| 11,029,788 | B2 * | 6/2021 | Park | G06F 3/0416 |
| 11,290,583 | B2 | 3/2022 | Hong et al. | |
| 11,641,416 | B2 | 5/2023 | Hong et al. | |
| 2003/0036685 | A1 * | 2/2003 | Goodman | G16H 70/20 600/300 |
| 2012/0029361 | A1 * | 2/2012 | Addison | A61B 5/02125 600/484 |
| 2014/0092064 | A1 | 4/2014 | Bernstein et al. | |
| 2017/0086686 | A1 | 3/2017 | Narasimhan et al. | |
| 2018/0365466 | A1 * | 12/2018 | Shim | G06V 40/67 |
| 2019/0076032 | A1 * | 3/2019 | Park | A61B 5/681 |
| 2019/0303639 | A1 * | 10/2019 | He | G09G 3/3208 |
| 2019/0310143 | A1 * | 10/2019 | Hong | G06F 3/0414 |
| 2020/0019745 | A1 * | 1/2020 | Kang | G06V 40/1318 |
| 2020/0093441 | A1 | 3/2020 | Himley | |
| 2020/0258957 | A1 * | 8/2020 | Kwak | H04N 23/57 |
| 2020/0383579 | A1 | 12/2020 | Young | |

FOREIGN PATENT DOCUMENTS

| | | |
|---|---|---|
| KR | 10-2018-0018318 | 2/2018 |
| KR | 10-2019-0020958 | 3/2019 |
| KR | 10-2020-0007312 | 1/2020 |
| KR | 10-2021-0012421 | 2/2021 |
| KR | 10-2021-0028302 A | 3/2021 |
| WO | WO 2020/251704 | 12/2020 |

OTHER PUBLICATIONS

Charles F. Babes, "Oscillometric Measurement of Systolic and Diastolic Blood Pressures Validated in Physiologic Mathematical Model," Biomedial Engineering Online 2012, 11:56.

* cited by examiner

DISPLAY DEVICE INCLUDING A FORCE SENSOR, A LIGHT RECEIVING SENSOR, AND A MAIN PROCESSOR

CROSS-REFERENCE TO RELATED APPLICATION

This application claims priority under 35. U.S.C. § 119 to Korean Patent Application No. 10-2021-0170958, filed on Dec. 2, 2021, in the Korean Intellectual Property Office, the disclosure of which is incorporated by reference herein in its entirety.

TECHNICAL FIELD

The present disclosure relates to a display device and, more specifically, to a display device including a force sensor, a light receiving sensor, and a main processor.

DISCUSSION OF THE RELATED ART

A display device is a device that displays an image on a screen. Display devices have been used not only for televisions and monitors, but also for portable devices like smartphones, tablets, personal computers (PCs), and the like. In the case of portable display devices, various functions can be included in the display device. For example, a camera and a fingerprint sensor may be included in the display device.

Recently, as the healthcare industry is in the spotlight, methods have been developed to facilitate obtaining biometric information related to health. For example, attempts have been made to replace a traditional blood pressure measuring device using an oscillometric method with a portable blood pressure measuring device. However, because a conventional portable blood pressure measuring device requires a separate light source, sensor, and display, it is necessary to separately carry the portable blood pressure measuring device in addition to the portable smartphone or tablet PC, which causes inconvenience.

SUMMARY

A display device includes a display panel including a plurality of pixels; a force sensor disposed on a surface of the display panel, the force sensor configured to sense an external force; a light receiving sensor disposed between a group of neighboring pixels of the plurality of pixels, or disposed in a through hole in a front portion of the display panel, the light receiving sensor configured to sense an amount of light reflected toward the display panel and generate an optical signal corresponding to the amount of the light; and a main processor configured to generate a pulse wave signal according to the optical signal received from the light receiving sensor and analyze a magnitude, a period, and a wave change of the pulse wave signal.

A method for using a display device includes receiving a force signal from a force sensor, the force sensor generating the force signal based on an external force; receiving an optical signal from a light receiving sensor, the optical signal sensing an amount of light and generating the optical signal corresponding to the amount of the light; generating, using a main processor, a pulse wave signal according to the optical signal; determining, using the main processor, a period of the pulse wave signal by identifying a wave period, wherein a highest pulse wave value, a reflected pulse wave value, and a lowest pulse wave value sequentially occur in the wave period; determining, using the main processor, a plurality of benchmarks including at least a pulse wave value ratio and a reflected pulse wave difference, wherein the pulse wave value ratio is determined based on a ratio of the reflected pulse wave value to the highest pulse wave value (RI ratio) during the period of the pulse wave signal, and the reflected pulse wave difference is determined based on a difference between a blood pressure at a time point when the highest pulse wave value is detected and a blood pressure at a time point when the reflected pulse wave value is detected; generating, using the main processor, benchmark data by continuously storing and measuring a change in a benchmark; detecting, using the main processor, a start time of the rapid change period and a start time of the second period by analyzing fluctuations of the benchmark; setting, using the main processor, a diastolic blood pressure according to a pulse wave signal detection value at the start time of the rapid change period; setting, using the main processor, a systolic blood pressure according to a pulse wave signal detection value at a start time of the second period after the rapid change period; and setting, using the main processor, a mean blood pressure according to a pulse wave signal detection value in either the first period or the second period.

BRIEF DESCRIPTION OF THE DRAWINGS

The above and other aspects and features of the present disclosure will be described in detail with reference to the accompanying drawings, in which.

DETAILED DESCRIPTION OF THE EMBODIMENTS

The exemplary embodiments of the present inventive concept are described hereinafter with reference to the accompanying drawings. This inventive concept may, however, be embodied in different forms and should not be construed as limited to the embodiments set forth herein. Rather, these embodiments are provided to convey the scope of the invention to those skilled in the art.

It will also be understood that when a layer is referred to as being "on" another layer or substrate, it can be directly on the other layer or substrate, or intervening layers may also be present. The same reference numbers indicate the same components throughout the specification.

It will be understood that, although the terms "first," "second," etc. may be used herein to describe various elements, these elements should not be limited by these terms. These terms are only used to distinguish one element from another element. For instance, a first element discussed below could be termed a second element without departing from the teachings of the exemplary embodiments of the present inventive concept. Similarly, the second element could also be termed the first element.

Each of the features of the various embodiments of the present disclosure may be combined or combined with each other, in part or whole, and technically various interlocking and driving are possible. Each embodiment may be implemented independently of each other or may be implemented together in an association.

Hereinafter, embodiments will be described in detail with reference to the accompanying drawings.

Figure 1:
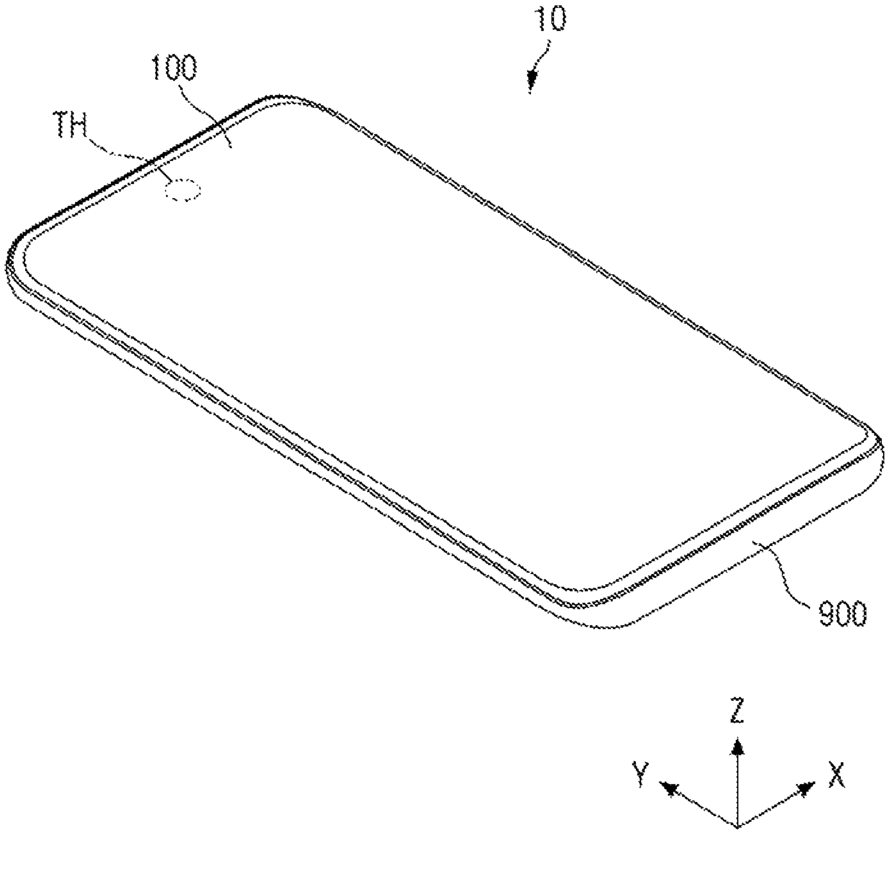
FIG. 1 is a schematic perspective view showing a display device according to an exemplary embodiment.
Figure 2:
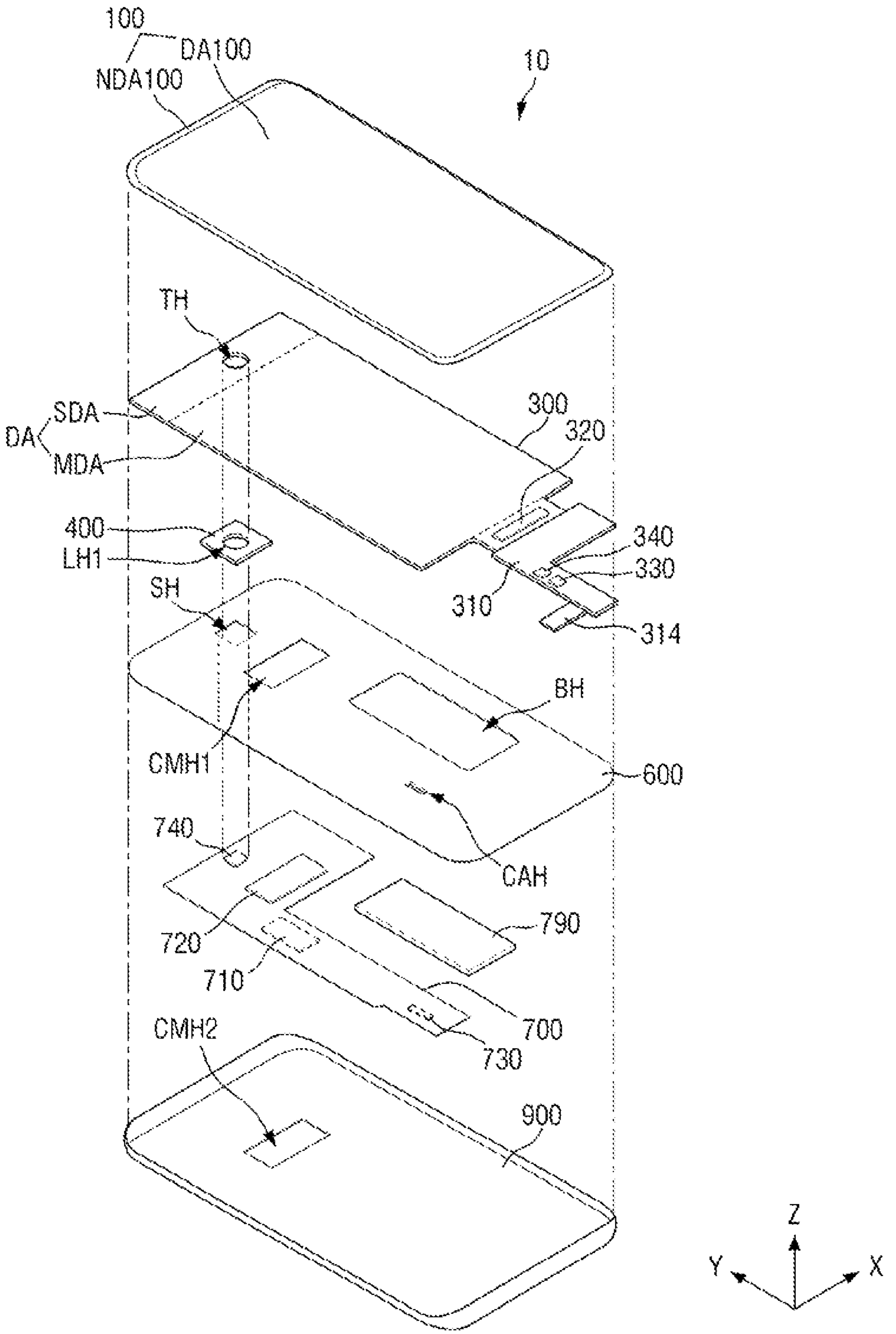
FIG. 2 is an exploded perspective view showing a display device according to an exemplary embodiment.

FIG. 1 is a schematic perspective view showing a display device according to one exemplary embodiment. FIG. 2 is an exploded perspective view showing a display device according to one exemplary embodiment.

Referring to FIGS. 1 and 2, a display device 10 comprises a plurality of pixels for displaying images. A display device 10 may be applied to electronic devices. For example, according to one exemplary embodiment, a display device 10 may be applied to portable electronic devices such as a mobile phone, a smartphone, a tablet personal computer, a mobile communication terminal, an electronic organizer, an electronic book, a portable multimedia player (PMP), a navigation system, an ultra mobile PC (UMPC) or the like. Alternatively, the display device 10 according to one exemplary embodiment may be applied as a display unit of a television, a laptop, a monitor, a billboard, or an Internet-of-Things (IoT) terminal.

Further, the display device 10 according to one exemplary embodiment of the present disclosure may be applied to wearable devices such as a smart watch, a watch phone, a glasses type display, or a head mounted display (HMD). Alternatively, the display device 10 according to one exemplary embodiment may be applied to a dashboard of a vehicle, a center fascia of a vehicle, a center information display (CID) disposed on a dashboard of a vehicle, a room mirror display in place of side mirrors of a vehicle, or a display disposed on a rear surface of a front seat for rear seat entertainment of a vehicle.

In some exemplary embodiments of the present disclosure, a first direction (X-axis direction) may be a short side direction of the display device 10, for example, a horizontal direction of the display device 10. A second direction (Y-axis direction) may be a long side direction of the display device 10, for example, a vertical direction of the display device 10. A third direction (Z-axis direction) may be a thickness direction of the display device 10.

The display device 10 may have a planar shape similar to a quadrilateral shape. In some cases, the display device 10 may have a planar shape similar to a rectangular shape. For example, the display device 10 may have short sides in the first direction (X-axis direction) and long sides in the second direction (Y-axis direction), as shown in FIG. 1. The corner where the short side in the first direction (X-axis direction) and the long side in the second direction (Y-axis direction) meet may be rounded to have a predetermined curvature. The corner may also be in other shapes, for example, right-angled. The planar shape of the display device 10 is not necessarily limited to a quadrilateral shape and may be formed in a shape similar to another polygonal shape, a circular shape, or an elliptical shape.

The display device 10 may be formed flat. Alternatively, the display device 10 may be formed such that the two sides of the display device 10 facing each other are bendable. For example, the display device 10 may be formed such that the left and right sides are bendable. Alternatively, the display device 10 may be formed such that all of the upper, lower, left, and right sides are bendable.

The display device 10 according to one exemplary embodiment includes a cover window 100, a display panel 300, a display circuit board 310, a display driving circuit 320, a bracket 600, a main circuit board 700, a light receiving sensor 740, and a lower cover 900.

The cover window 100 may be disposed above the display panel 300 to be in contact with and cover the front surface of the display panel 300. Accordingly, the cover window 100 may function to protect the front surface of the display panel 300.

The cover window 100 may include a light transmitting portion DA100 corresponding to the display panel 300 and a light blocking portion NDA100 corresponding to an area other than the display panel 300. The light blocking portion NDA100 may be formed to be opaque. Alternatively, the light blocking portion NDA100 may be formed as a decorative layer having a pattern that can be displayed to the user when an image is not displayed.

The display panel 300 may be disposed below the cover window 100. The display panel 300 may include a display area DA and a non-display area NDA. The display area DA may be an area including pixels displaying an image, and the non-display area NDA may be an area in which an image is not displayed, as a peripheral area of the display area DA. The non-display area NDA may not include pixels. The non-display area NDA may be disposed to at least partially surround the display area DA as shown in FIG. 2, but is not necessarily limited thereto.

The display panel 300 may include a through hole TH. The through hole TH may be a hole penetrating the display panel 300. The through hole TH may be arranged to be at least partially surrounded by the display area DA.

The through hole TH may overlap a sensor hole SH of the bracket 600 and the light receiving sensor 740 in the third direction (Z-axis direction). Accordingly, in some cases, light having passed through the through hole TH of the display panel 300 may be incident on the light receiving sensor 740 through the sensor hole SH. Therefore, the light receiving sensor 740 disposed under the display panel 300 may sense the light incident from the front surface of the display device 10.

FIG. 2 illustrates the display panel 300 including a through hole TH. In some cases, the number of through holes TH is not necessarily limited thereto. When the display panel 300 includes a plurality of through holes TH. A through holes TH may overlap the light receiving sensor 740 in the third direction (Z-axis direction), while the other through holes TH may overlap sensor units other than the light receiving sensor 740. For example, the sensor units may be proximity sensors, illuminance sensors, or front camera sensors.

The display panel 300 may be a light emitting display panel including a light emitting Component. For example, the display panel 300 may be an organic light emitting display panel using an organic light emitting diode including an organic light emitting layer, a micro light emitting diode display panel using a micro LED, a quantum dot light emitting display panel using a quantum dot light emitting diode including a quantum dot light emitting layer, or an inorganic light emitting display panel using an inorganic light emitting component including an inorganic semiconductor. The following description is directed to the case where the display panel 300 is an organic light emitting display panel.

According to one exemplary embodiment of the present disclosure, the display panel 300 may include a touch electrode layer having touch electrodes for sensing an object such as a human finger, a pen, or the like. In this case, the touch electrode layer may be disposed on a display layer on which pixels displaying an image are arranged. The display layer and the touch electrode layer will be specifically described later with reference to FIG. 7.

The display circuit board 310 and the display driving circuit 320 may be attached to one side of the display panel 300. The display circuit board 310 may be a flexible printed circuit board that is bendable, a rigid printed circuit board that is solid to be hardly bent, or a composite printed circuit board having both the rigid printed circuit board and the flexible printed circuit board.

The display driving circuit 320 may receive control signals and power voltages through the display circuit board 310 to generate and output signals and voltages for driving the display panel 300. In some cases, the display driving circuit 320 may be formed of an integrated circuit (IC) to be attached on the display panel 300. For example, the integrated circuit (IC) may be attached on the display panel 300 by a chip-on-glass (COG) method, a chip-on-plastic (COP) method, or an ultrasonic bonding method, but the present disclosure is not necessarily limited thereto. In some cases, the display driving circuit 320 may be attached onto the display circuit board 310.

A touch driving circuit 330 and a force driving circuit 340 may be disposed on the display circuit board 310. In some cases, the touch driving circuit 330 or the force driving circuit 340 may separately be formed of an IC. For example, the IC may be attached to the top surface of the display circuit board 310. Alternatively, the touch driving circuit 330 and the force driving circuit 340 may be integrally formed as one IC in some other cases.

The touch driving circuit 330 may be electrically connected to the touch electrodes of the touch electrode layer of the display panel 300 through the display circuit board 310. The touch driving circuit 330 may output a touch driving signal to the touch electrodes and sense the voltage charged in the capacitances of the touch electrodes.

The touch driving circuit 330 may generate touch data according to the change in the electrical signal sensed at each of the touch electrodes to transmit the touch data to a main processor 710. Then, the main processor 710 may analyze the touch data to generate touch coordinates. The touch may include a contact touch and a proximity touch. The contact touch may indicate that the object such as the human finger or pen makes direct contact with the cover window disposed above the touch electrode layer. The proximity touch indicates that the object such as the human finger or pen is positioned above the cover window to be proximately apart therefrom, such as hovering.

The force driving circuit 340 may detect an electrical signal from a force sensor electrode of a force sensor 400 to convert the detected signal into force data and transmit it to the main processor 710. The main processor 710 may determine whether a force has been applied to the force sensor 400 or not, and may calculate the magnitude of the force applied to the force sensor 400 based on the force data.

Further, a power supply unit may be additionally disposed on the display circuit board 310 to supply display driving voltages for driving the display driving circuit 320.

The bracket 600 may be disposed under the display panel 300. The bracket 600 may include plastic, metal, or both plastic and metal. The bracket 600 may include a first camera hole CMH1 into which a first camera sensor 720 is inserted, a battery hole BH in which a battery is disposed, a cable hole CAH through which a cable 314 connected to the display circuit board 310 passes, and the sensor hole SH overlapping the light receiving sensor 740 in the third direction (Z-axis direction). In this case, the light receiving sensor 740 may be arranged in the sensor hole SH. Alternatively, the bracket 600 may be formed so as not to overlap a sub-display area SDA of the display panel 300 without including the sensor hole SH.

The main circuit board 700 and a battery 790 may be disposed under the bracket 600. The main circuit board 700 may be a printed circuit board or a flexible printed circuit board.

The main circuit board 700 may include a main processor 710, a first camera sensor 720, a main connector 730, and the light receiving sensor 740. The first camera sensor 720 may be disposed on both the top and bottom surfaces of the main circuit board 700, the main processor 710 may be disposed on the top surface of the main circuit board 700, and the main connector 730 may be disposed on the bottom surface of the main circuit board 700. The light receiving sensor 740 may be disposed on the top surface of the main circuit board 700.

The main processor 710 may control the display device 10. For example, the main processor 710 may output digital video data to the display driving circuit 320 through the display circuit board 310 such that the display panel 300 displays an image. In one example, the main processor 710 may receive touch data from the touch driving circuit 330 and determine the user's touch coordinates, and then execute an application indicated by an icon displayed on the user's touch coordinates. In one example, the main processor 710 may convert the first image data inputted from the first camera sensor 720 into digital video data and output it to the display driving circuit 320 through the display circuit board 310, thereby displaying an image captured by the first camera sensor 720 on the display panel 300. In one example, the main processor 710 may calculate a pulse wave signal reflecting a change in blood flow corresponding to heartbeats, according to an optical signal inputted from the light receiving sensor 740. Then, a user's blood pressure may be measured using an analysis result of the pulse wave signal based on the pulse wave signal.

The first camera sensor 720 may process a still image or an image frame of a video obtained from the image sensor and output it to the main processor 710. The first camera sensor 720 may be a complementary metal-oxide-semiconductor (CMOS) image sensor or a charge-coupled device (CCD) sensor. The CMOS and the CCD can be configured to sense light. The first camera sensor 720 may be exposed to the bottom surface of the lower cover 900 by a second camera hole CMH2 to thereby capture an image of a background or an object disposed below the display device 10.

The cable 314 is disposed through the cable hole CAH of the bracket 600. The cable 314 may be connected to the main connector 730. Thus, the main circuit board 700 may be electrically connected to the display circuit board 310.

The light receiving sensor 740 may include a light receiving component capable of sensing light incidents through the through hole TH. In this case, the light receiving component may be a photodiode or phototransistor. For example, the light receiving sensor 740 may be a CMOS image sensor or a CCD sensor The light receiving sensor 740 may output an optical signal to the main processor 710 according to the amount of light reflected from an object disposed above the through hole TH. The main processor 710 may calculate or generate a pulse wave signal reflecting a change in blood flow according to heartbeats, according to the optical signal. In some cases, the main processor 710 may measure the user's blood pressure by analyzing at least one of the following: a signal value at a specific time point, an amplitude (or a magnitude), a pulse width, a period, and a wave change of the pulse wave signal. As such, a method of measuring a user's blood pressure based on the pulse wave signal will be described later with reference to FIGS. 4, 5, and the like.

The battery 790 may be disposed so as not to overlap the main circuit board 700 in the third direction (Z-axis direction). The battery 790 may overlap the battery hole BH of the bracket 600.

In addition, the main circuit board 700 may be further equipped with a mobile communication module capable of transmitting and receiving radio signals with at least one of a base station, an external terminal, or a server in a mobile communication network. The radio signal may include various types of data according to transmission and reception of a voice signal, a video call signal, or a text/multimedia message.

In one exemplary embodiment, the lower cover 900 may be disposed below the main circuit board 700 and the battery 790. The lower cover 900 may be fixed by being fastened to the bracket 600. The lower cover 900 may form an external appearance of the bottom surface of the display device 10. The lower cover 900 may include plastic, metal, or both plastic and metal.

In one exemplary embodiment, the second camera hole CMH2 exposing the bottom surface of the first camera sensor 720 may be formed in the lower cover 900. The positions of the first camera sensor 720 and the positions of the first and second camera holes CMH1 and CMH2 corresponding to the first camera sensor 720 are not necessarily limited to the embodiment illustrated in FIG. 2.

Figure 3:
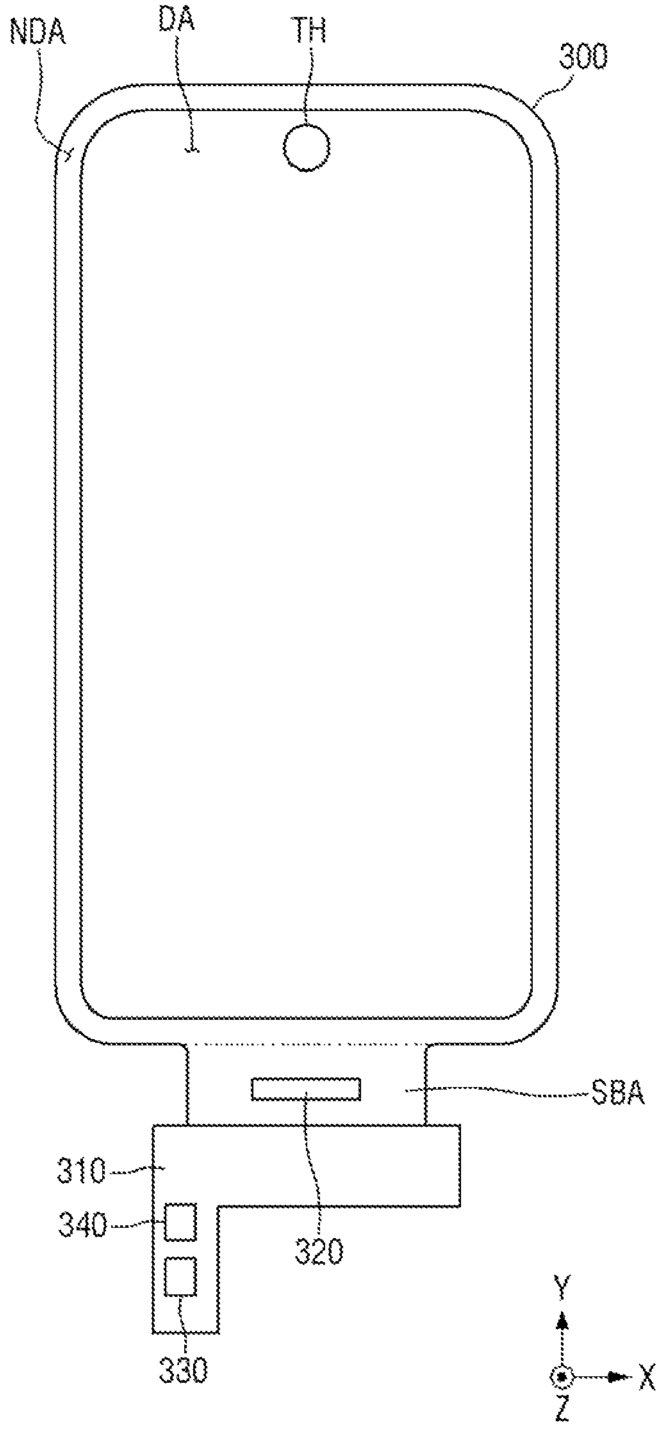
FIG. 3 is a plan view illustrating a display panel, a display circuit board, a display driving circuit, and a touch driving circuit according to an exemplary embodiment.

FIG. 3 is a plan view illustrating a display panel, a display circuit board, a display driving circuit, and a touch driving circuit according to one exemplary embodiment.

Referring to FIG. 3, the display panel 300 may be a rigid display panel that is rigid not to be easily bent or a flexible display panel that is flexible to be easily bent, folded, or rolled up. For example, the display panel 300 may be a foldable display panel which can be folded and unfolded, a curved display panel having a curved display surface, a bended display panel having a bent area other than the display surface, a rollable display panel which can be rolled up and rolled out and a stretchable display panel which can be stretched.

In one exemplary embodiment, the display panel 300 may be transparent. The display panel 300 may be implemented as transparent to allow an object or a background disposed behind the rear surface of the display panel 300 to be viewed from the front surface of the display panel 300. In some cases, the display panel 300 may be a reflective display panel capable of reflecting an object or background in front of the front surface of the display panel 300.

The display panel 300 may include a main region MA and a sub-region SBA protruding from one side of the main region MA. The main region MA may include a display area DA displaying an image and a non-display area NDA that is a peripheral area of the display area DA. The display area DA may occupy most of the main region MA. The display area DA may be disposed at the center of the main region MA. The non-display area NDA may be an area outside the display area DA. The non-display area NDA may be defined as an edge area of the display panel 300.

The display panel 300 may include a through hole TH. The through hole TH may be a hole penetrating the display panel 300. FIG. 3 illustrates that the through hole TH is a hole penetrating the display panel 300, that is, a physically formed hole, but the present disclosure is not necessarily limited thereto. The through hole TH may be an optical hole through which light may pass. Alternatively, the through hole TH may have a form in which a physical hole and an optical hole are mixed.

Since the through hole TH overlaps the light receiving sensor 740 in the third direction (Z-axis direction) as shown in FIG. 2, light having passed through the through hole TH may be incident on the light receiving sensor 740. Accordingly, the light receiving sensor 740 may sense the light incident from the front surface of the display device 10 even though the light receiving sensor 740 is disposed to overlap the display panel 300 in the third direction (Z-axis direction). For example, the light receiving sensor 740 may sense light reflected from an object disposed above the through hole TH.

The through hole TH may be disposed to be at least partially surrounded by the display area DA. Alternatively, the through hole TH may be disposed to be at least partially surrounded by the non-display area NDA or may be disposed between the display area DA and the non-display area NDA. In addition, although FIG. 2 illustrates that the through hole TH is disposed at the upper center of the display panel 300, the arrangement position of the through hole TH is not necessarily limited thereto.

The sub-region SBA may protrude in the second direction (Y-axis direction) from one side of the main region MA. As illustrated in FIG. 2, the length of the sub-region SBA in the first direction (X-axis direction) may be smaller than the length of the main region MA in the first direction (X-axis direction), and the length of the sub-region SBA in the second direction (Y-axis direction) may be smaller than the length of the main region MA in the second direction (Y-axis direction), but the present disclosure is not necessarily limited thereto. The sub-region SBA may be foldable to be disposed under the display panel 300. In this case, the sub-region SBA may overlap the main region MA in the third direction (Z-axis direction).

The sub-region SBA of the display panel 300 may be foldable to be placed under the display panel 300 as shown in FIG. 2. In this case, the sub-region SBA of the display panel 300 may overlap the main region MA of the display panel 300 in the third direction (Z-axis direction).

The display circuit board 310 and the display driving circuit 320 may be attached to the sub-region SBA of the display panel 300. The display circuit board 310 may be attached onto pads of the sub-region SBA of the display panel 300 using some materials. For example, a low resistance and high reliability material such as an anisotropic conductive film, a self assembly anisotropic conductive paste (SAP) or the like can be used. The touch driving circuit 330 may be disposed on the display circuit board 310.

Figure 4:
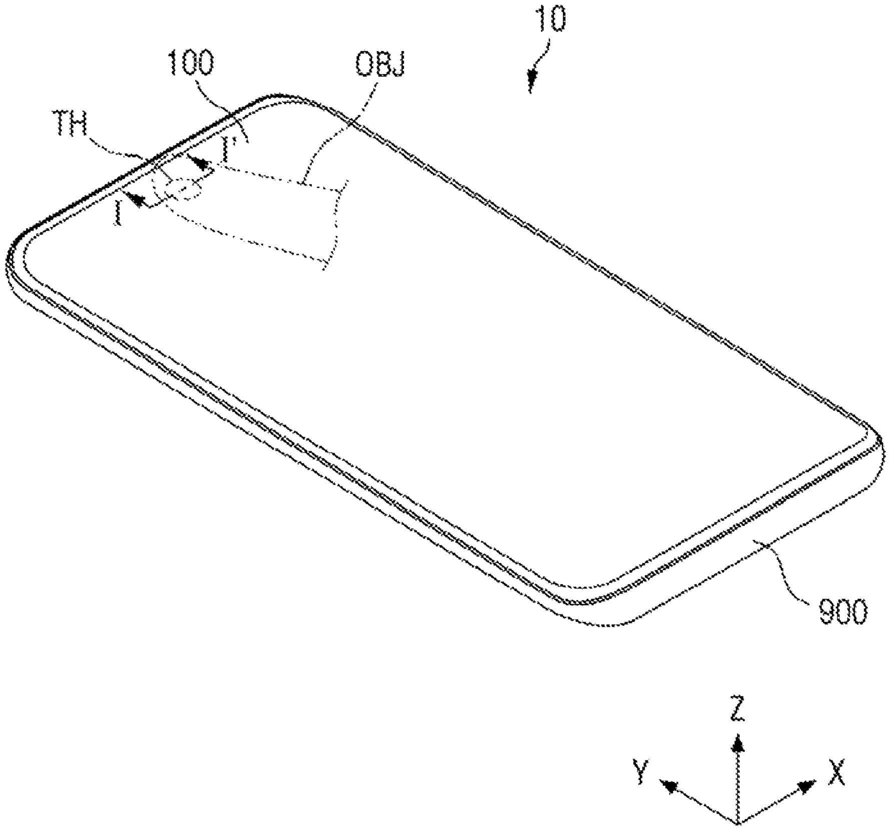
FIG. 4 is a schematic perspective view showing the display device measuring a blood pressure according to an exemplary embodiment.
Figure 5:
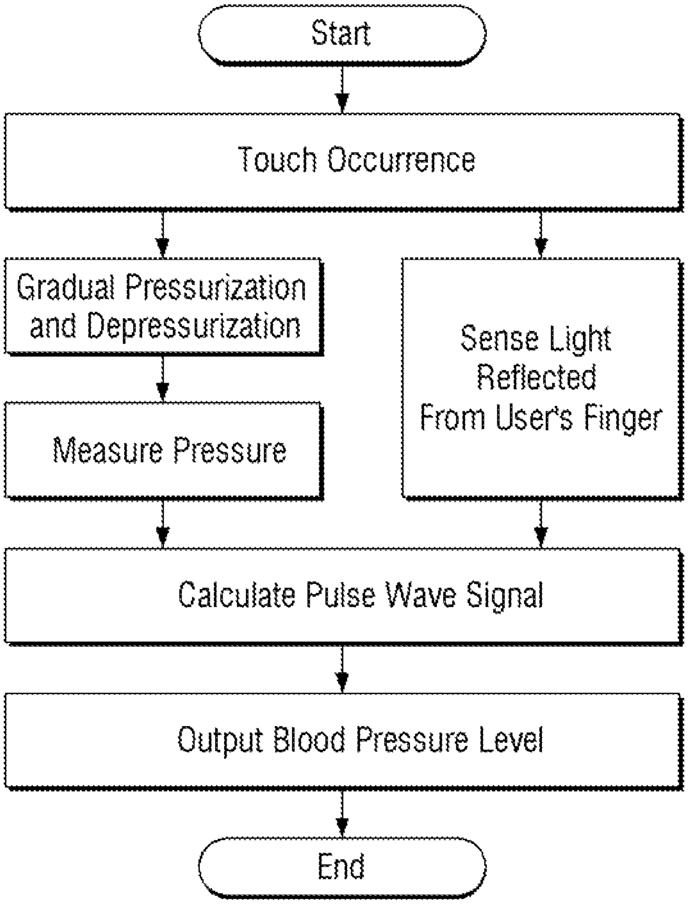
FIG. 5 is a flowchart illustrating a method of measuring a blood pressure by the display device according to one exemplary embodiment.

FIG. 4 is a schematic perspective view showing the display device measuring a blood pressure according to one exemplary embodiment. FIG. 5 is a flowchart illustrating a method of measuring a blood pressure by the display device according to one exemplary embodiment.

Referring to FIGS. 4 and 5, when a user's body part, for example, a finger OBJ touches the front surface of the display device 10, the display device 10 may recognize that a touch has occurred. The display device 10 may recognize the user's touch using the touch electrode layer of the display panel 300, or the force sensor 400.

The blood pressure measurement mode of the display device 10 can be activated in multiple ways. For example, when the display device 10 determines that a touch has occurred, the display device 10 may operate in a blood pressure measurement mode. The blood pressure measurement mode can also be set without a touch. For example, the user can set the blood pressure measurement mode through a program or application of the display device 10 before measuring a blood pressure, and the display device 10 will perform blood pressure measurement according to the touch occurrence. Alternatively, the display device 10 may automatically switch to the blood pressure measurement mode after a touch occurs without requiring the user's additional input action for mode determination. When the user touches a position which is out of the blood pressure measurement position, the display device 10 may operate in a touch mode. In some cases, when the user touches a position which corresponds to the blood pressure measurement position, the display device 10 may operate in the blood pressure measurement mode. In addition, when the user increases a touch force, the display device 10 may operate in the blood pressure measurement mode by force analysis of the force sensor 400.

In the blood pressure measurement mode, the display device 10 may measure the blood pressure by using both the light receiving sensor 740 and the force sensor 400.

Figure 6:
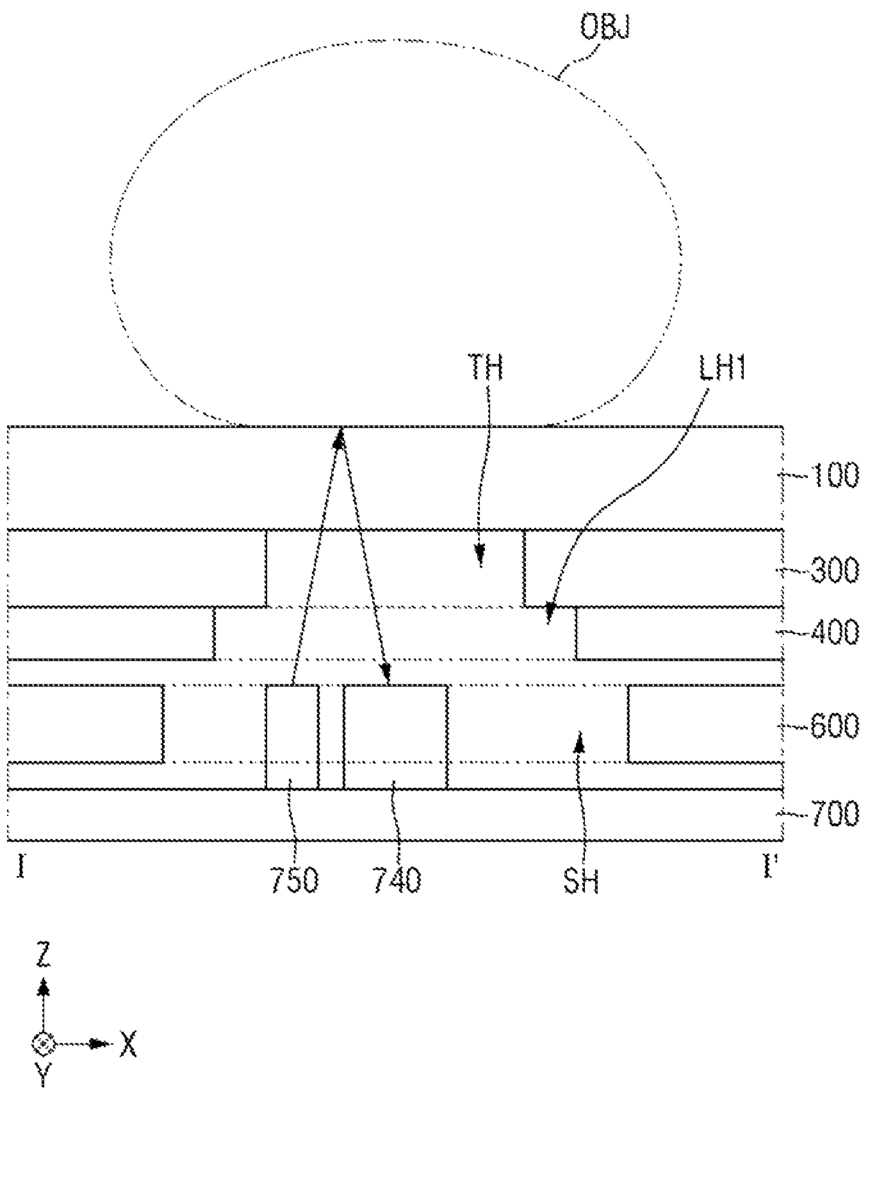
FIG. 6 is a cross-sectional view illustrating structures of a cover window, a display panel, a force sensor, a light emitting member, and a light receiving sensor taken along line I-I' of FIG. 4.

As shown in FIG. 6, an amount of light reflected from the user's finger OBJ among lights outputted from a light emitting member 750, after passing through the through hole TH, may be sensed by the light receiving sensor 740 The amount of light reflected from the user's finger OBJ can be associated with some of the user's bodily movements, for example, heart contractions. When a heart contracts, blood ejected from a left ventricle of the heart moves to peripheral tissues, which increases the arterial blood volume. Further, when the heart contracts, red blood cells carry more oxygen hemoglobin to the peripheral tissues. When the heart relaxes, the heart receives a partial influx of blood from the peripheral tissues. In this example, when light is irradiated to peripheral blood vessels, the irradiated light is absorbed by the peripheral tissues. Light absorbance depends on hematocrit and blood volume. Accordingly, the light absorbance may have a maximum value when the heart contracts and may have a minimum value when the heart relaxes. Therefore, an amount of light sensed by the light receiving sensor 740 may have a minimum value when the heart contracts and may have a maximum value when the heart relaxes.

Further, when the user puts a finger on the display device 10 and lifts it off in the blood pressure measurement mode, a force (contact force) applied to the force sensor 400 may gradually increase to reach a maximum value, and may gradually decrease. When the contact force increases, blood vessels may be narrowed, resulting in no blood flow. When the contact force decreases, the blood vessels expand, and thus blood flows again. A further decrease of the contact force results in greater blood flow. Therefore, the amount of light sensed by the light receiving sensor 740 may correspond to the blood flow. For example, the change in the amount of light sensed may be proportional to the change in blood flow.

The main processor 710 may generate the pulse wave signal according to the force applied by the user, based on a force value calculated by the force sensor 400 and the optical signal according to the amount of light sensed by the light receiving sensor 740. Further, the main processor 710 may calculate the blood pressure based on the pulse wave signal. The pulse wave signal may have a waveform vibrating according to the cardiac cycle. For example, the main processor 710 may estimate blood pressure values of the blood vessels of the finger OBJ of the user based on a time difference between a time point corresponding to the maximum value of the calculated pulse wave signal and a time point corresponding to any one of the maximum, minimum, and average values of the filtered pulse wave. Among the estimated blood pressure values, a maximum blood pressure value may be determined as a systolic blood pressure value, and a minimum blood pressure value may be determined as a diastolic blood pressure value. Further, some other blood pressure values, such as an average blood pressure value or the like, may be calculated using the estimated blood pressure values. The calculated blood pressure value may be displayed on the display area DA of the display device 10 to be provided to the user. As such, a method of measuring and displaying a user's blood pressure based on the pulse wave signal will be described later in more detail, in conjunction with FIGS. 11 to 25 and the like.

FIGS. 4 and 5 illustrate the user's finger OBJ as the user's body part where the blood pressure is measured, but the present disclosure is not necessarily limited thereto. For example, the user's body part where the blood pressure is measured may be a wrist or other body parts.

FIG. 6 is a cross-sectional view illustrating structures of a cover window, a display panel, a force sensor, a light emitting member, and a light receiving sensor taken along line I-I' of FIG. 4. FIG. 6 omits the lower cover 900 for convenience of illustration.

Referring to FIG. 6, the display device 10 may further include the force sensor 400, a polarizing film 500, and the light emitting member 750.

In one exemplary embodiment, the force sensor 400 may be disposed on one surface of the display panel 300. For example, the force sensor 400 may be disposed on the bottom surface of the display panel 300. In this case, the top surface of the force sensor 400 may be attached to the bottom surface of the display panel 300, for example, via a transparent adhesive member.

The force sensor 400 may be disposed to overlap the display area DA of the display panel 300 in the third direction (Z-axis direction). For example, the force sensor 400 may overlap the display area DA of the display panel 300 in the third direction (Z-axis direction). Alternatively, a portion of the force sensor 400 may overlap the display area DA of the display panel 300 in the third direction (Z-axis direction), and the remaining portion may overlap the non-display area NDA of the display panel 300 in the third direction (Z-axis direction).

The force sensor 400 may include a first optical hole LH1. The first optical hole LH1 may be an optical hole through which light may pass. Alternatively, the first optical hole LH1 may be a physically formed hole (physical hole), such as a hole penetrating the force sensor 400. Alternatively, the first optical hole LH1 may have a form in which a physical hole and an optical hole are mixed.

The first optical hole LH1 of the display panel 300 may overlap the sensor hole SH of the force sensor 400. The size of the through hole TH of the display panel 300 may be smaller than the size of the first optical hole LH1 of the force sensor 400. The length of the through hole TH in a direction may be smaller than the length of the first optical hole LH1 in the direction. For example, as illustrated in FIG. 6, the length of the through hole TH in the first direction (X-axis direction) may be smaller than the length of the first optical hole LH1 in the first direction (X-axis direction). Therefore, light having passed through the through hole TH may be incident on the light receiving sensor 740 overlapping the through hole TH in the third direction (Z-axis direction) without being blocked by the force sensor 400.

The polarization film may be disposed between the display panel 300 and the cover window 100. The polarization film may include a first base member, a linear polarization plate, a quarter-wave plate (λ/4 plate), a half-wave plate (λ/2 plate), and a second base member. In this case, the first base member, the λ/4 plate, the λ/2 plate, the linear polarization plate, and the second base member may be sequentially stacked on the display panel 300.

The bracket 600 may be disposed on one surface of the force sensor 400. For example, the bracket 600 may be disposed on the lower surface of the force sensor 400. The bracket 600 may include the sensor hole SH which is the physical hole penetrating the bracket 600. Alternatively, the sensor hole SH may be, for example, an optical hole capable of passing light. Alternatively, the sensor hole SH may have a shape in which the physical hole and the optical hole are mixed.

The through hole TH of the display panel 300 may overlap the sensor hole SH of the bracket 600. The size of the through hole TH of the display panel 300 may be smaller than the size of the sensor hole SH of the bracket 600. The length of the through hole TH in a direction may be smaller than the length of the sensor hole SH in the direction. For example, as illustrated in FIG. 6, the length of the through hole TH in the first direction (X-axis direction) may be smaller than the length of the sensor hole SH in the first direction (X-axis direction).

Further, the first optical hole LH1 of the force sensor 400 may overlap the sensor hole SH of the bracket 600. The size of the first optical hole LH1 of the force sensor 400 may be smaller than the size of the sensor hole SH of the bracket 600. The length of the first optical hole LH1 in a direction may be smaller than the length of the sensor hole SH in the direction. For example, as illustrated in FIG. 6, the length of the first optical hole LH1 in the first direction (X-axis direction) may be smaller than the length of the sensor hole SH in the first direction (X-axis direction). Therefore, light having passed through the through hole TH and the first optical hole LH1 may be incident on the light receiving sensor 740 overlapping the through hole TH in the third direction (Z-axis direction) without being blocked by the bracket 600.

The light emitting member 750 may include a light source that emits light. The light source may have, for example, at least one of the following: a light emitting diode (LED), an organic light emitting diode (OLED), a laser diode (LD), quantum dots (QD), or a phosphor.

The wavelength of light emitted from the light emitting member 750 may be, for example, an infrared wavelength, a visible wavelength, a wavelength of red light, or a wavelength of green light. Here, when the body part placed on the through hole TH is the finger OBJ whose blood vessels are fine, the wavelength of the light emitted from the light emitting member 750 may be the infrared wavelength or the wavelength of red light. In this case, since the infrared wavelength or the wavelength of red light is longer than the wavelength of green light or a wavelength of blue light, it is easy for the light to enter the blood vessels of the finger to be absorbed. In addition, when the body part placed on the through hole TH is the wrist, the artery of the wrist is sufficiently thick. Therefore, even in the case where the wavelength of the light emitted from the light emitting member 750 is the wavelength of green light, the green light may enter the artery of the wrist to be absorbed. In this manner, the wavelength of the light emitted from the light emitting member 750 may be determined according to the body part subjected to blood pressure measurement.

The light receiving sensor 740 and the light emitting member 750 may be disposed on one surface of the main processor 710. For example, the light receiving sensor 740 and the light emitting member 750 may be mounted on the top surface of the main processor 710.

The light receiving sensor 740 and the light emitting member 750 may overlap the through hole TH in the third direction (Z-axis direction). The light receiving sensor 740 and the light emitting member 750 may be arranged in the sensor hole SH of the bracket 600. Further, when the lengths of the light receiving sensor 740 and the light emitting member 750 are relatively long in the third direction (Z-axis direction), the light receiving sensor 740 and the light emitting member 750 may be disposed in the first optical hole LH1 of the force sensor 400, or in both the through hole TH of the display panel 300 and the first optical hole LH1 of the force sensor 400. In this case, both the through hole TH of the display panel 300 and the first optical hole LH1 of the force sensor 400 may be the physical holes.

As illustrated in FIG. 6, the light emitted from the light emitting member 750 may pass through the first optical hole LH1 of the force sensor 400 and the through hole TH of the display panel 300 to be absorbed by or reflected from the blood vessel of the user's finger OBJ. For example, the light reflected from the blood vessel of the user's finger OBJ may pass through the through hole TH of the display panel 300 and the first optical hole LH1 of the force sensor 400 to be sensed by the light receiving sensor 740.

Figure 7:
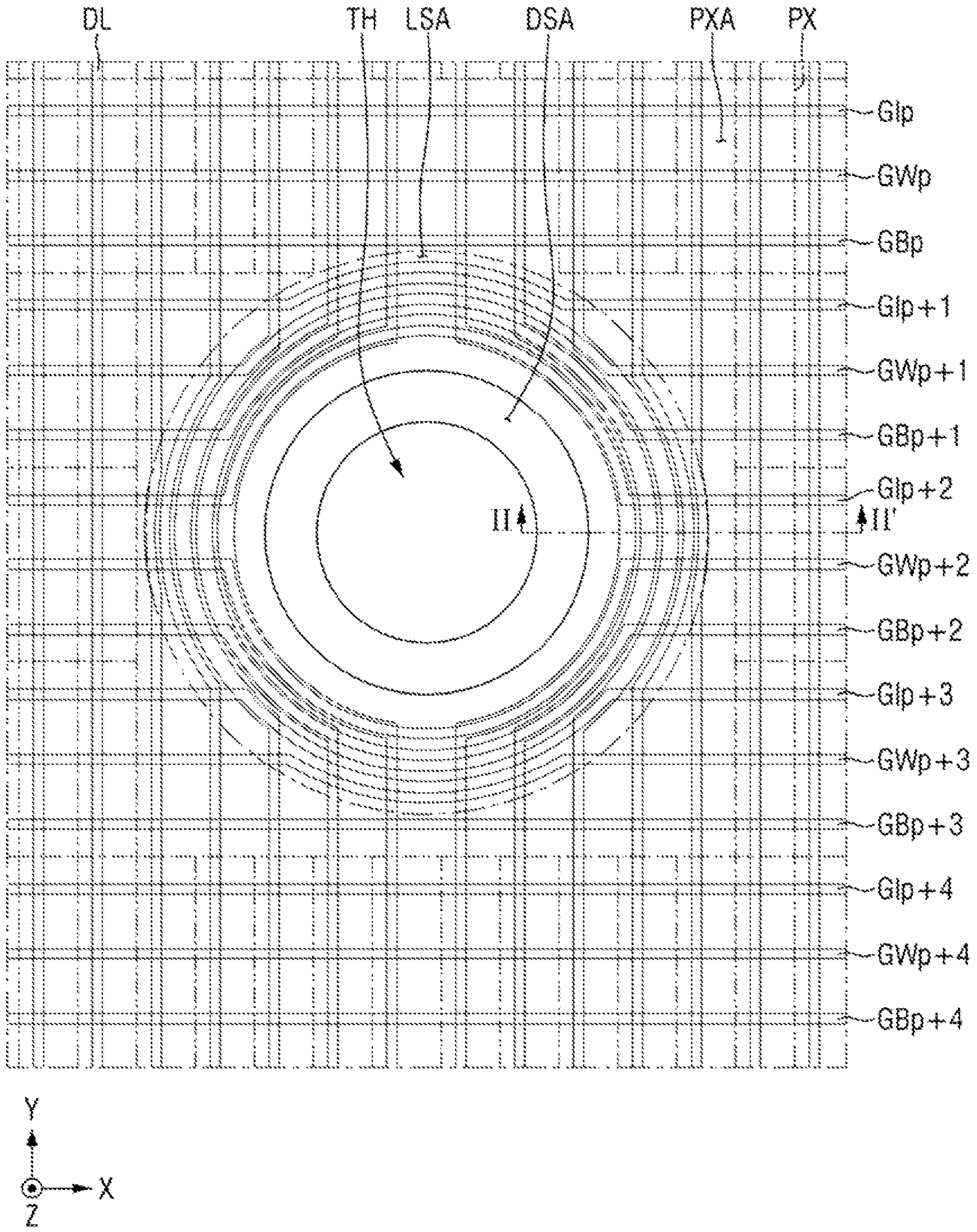
FIG. 7 is a layout view showing a display area and a through hole of a display panel according to one exemplary embodiment.

FIG. 7 is a layout view showing a display area and a through hole of a display panel according to one exemplary embodiment.

Referring to FIG. 7, the display area DA may include the through hole TH, a dead space area DSA, a wiring area LA, and a pixel area PXA.

The dead space area DSA may be arranged to at least partially surround the through hole TH. In some cases, Pixels PX, scan lines SL, and data lines DL are not disposed in the dead space area DSA. There are no pixels for display in the dead space area DSA. The dead space area DSA can be configured to prevent the through hole TH from entering the wiring area LA due to a process error in the through hole TH forming process.

The wiring area LA may be disposed to at least partially surround the dead space area DSA. Since the pixels PX are not disposed in the wiring area LA, the wiring area LA is an example of a non-display area that does not display an image.

The scan lines and the data lines DL that bypass the through hole TH may be disposed in the wiring area LA. The scan lines may include first initialization scan lines Gip to Gip+4, write scan lines GWp to GWp+4, and second initialization scan lines GBp to GBp+4.

The first initialization scan lines Gip to Gip+4, the write scan lines GWp to GWp+4, and the second initialization scan lines GBp to GBp+4 may extend in the first direction (X-axis direction). The first initialization scan lines Gip to Gip+4, the write scan lines GWp to GWp+4, and the second initialization scan lines GBp to GBp+4 may be curved in the second direction (Y-axis direction) to bypass the through hole TH. For example, among the first initialization scan lines Gip to Gip+4, the write scan lines GWp to GWp+4, and the second initialization scan lines GBp to GBp+4, scan lines that bypass the through hole TH to the upper side thereof may be curved in the upper direction. In another example, among the first initialization scan lines Gip to Gip+4, the write scan lines GWp to GWp+4, and the second initialization scan lines GBp to GBp+4, scan lines that bypass the through hole TH to the lower side thereof may be curved in the lower direction. Alternatively, the first initialization scan lines Gip to Gip+4, the write scan lines GWp to GWp+4, and the second initialization scan lines GBp to GBp+4 may be bent in the form of a staircase to bypass the through hole TH.

The data lines DL may extend in the second direction (Y-axis direction). The data lines DL may be curved in the first direction (X-axis direction) to bypass the through hole TH. For example, among the data lines DL, lines that bypass the through hole TH to the left side thereof may be curved in the left direction. In another example, among the data lines DL, lines that bypass the through hole TH to the right side thereof may be curved in the right direction. Alternatively, the data lines DL may be bent in the form of, for example, a staircase to bypass the through hole TH.

A distance between the scan lines adjacent to each other in the wiring area LA may be smaller than that in the pixel area PXA. Further, a distance between the data lines DL adjacent to each other in the wiring area LA may be smaller than that in the pixel area PXA. Furthermore, in the wiring area LA, the scan lines may overlap the data lines DL in the third direction (Z-axis direction).

Each of the pixels PX may overlap any one of the first initialization scan lines Gip to Gip+4, any one of the write scan lines GWp to GWp+4, and any one of the second initialization scan lines GBp to GBp+4, and any one of the data lines DL.

As illustrated in FIG. 7, the scan lines and the data lines DL are designed to bypass the through hole TH in the wiring area LA, and the pixels PX are not arranged in the wiring area LA. Accordingly, when the through hole TH is disposed to penetrate the display area DA of the display panel 300, the display panel 300 may be configured to display an image.

Figure 8:
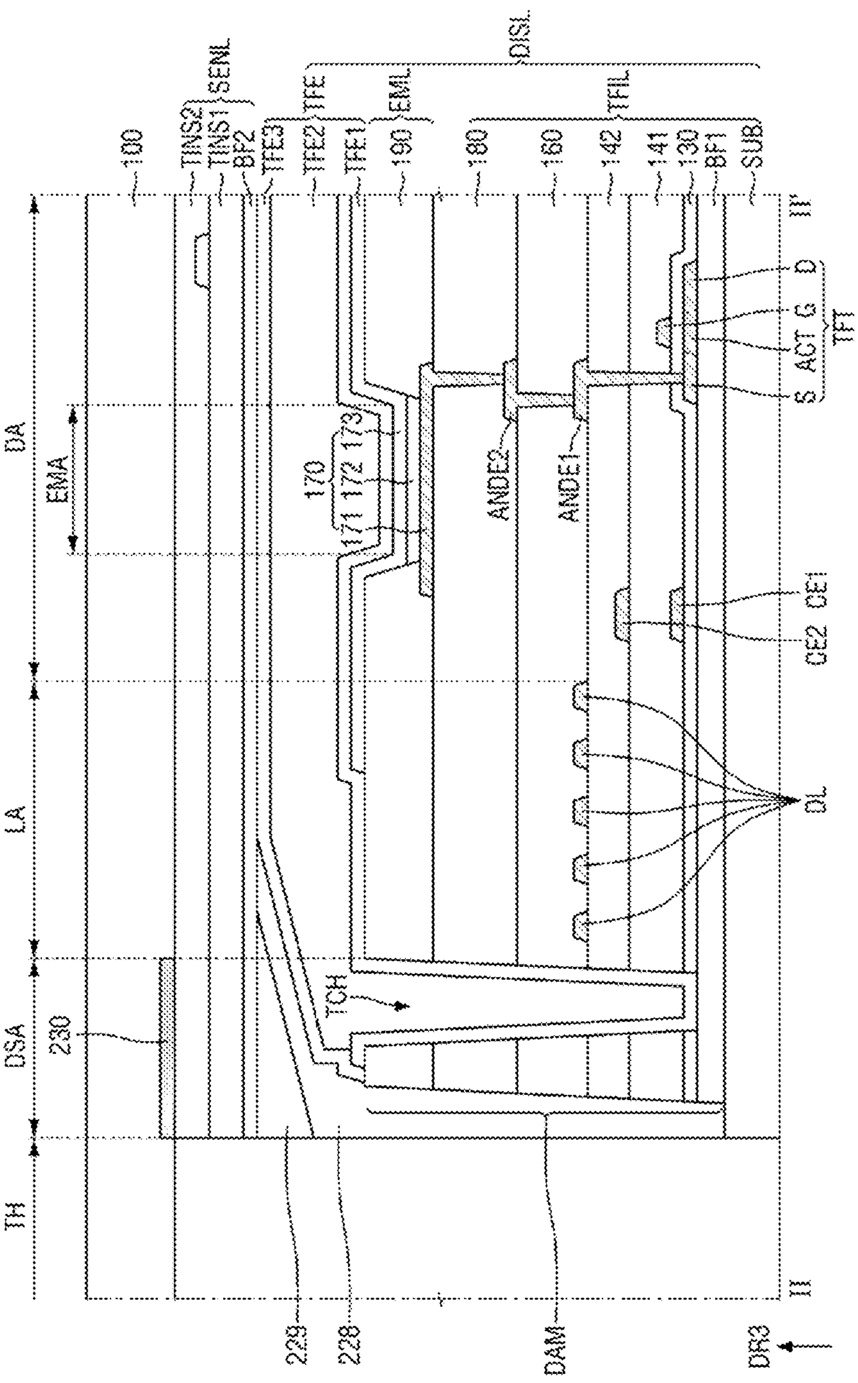
FIG. 8 is a cross-sectional view illustrating a structure of a display panel taken along lines II-II' of FIG. 7.

FIG. 8 is a cross-sectional view illustrating a structure of a display panel taken along lines II-II' of FIG. 7.

Referring to FIG. 8, a first buffer layer BF1, a thin film transistor layer TFTL, a light emitting component layer EML, an encapsulation layer TFE, and a touch electrode layer SENL. May be sequentially disposed on the substrate SUB in that order.

The substrate SUB may be formed of an insulating material such as glass, quartz, or a polymer resin. For example, the substrate SUB may include polyimide. The substrate SUB may be a flexible substrate which can be, for example, bent, folded or rolled.

The first buffer layer BF1 is a film for protecting thin film transistors TFT of the thin film transistor layer TFTL and a light emitting layer 172 of the light emitting component layer EML from moisture permeating through the substrate SUB which is susceptible to moisture permeation. The first buffer layer BF1 may be formed of a plurality of inorganic layers that are alternately stacked. For example, the first buffer layer BF1 may be formed of multiple layers in which one or more inorganic layers of a silicon nitride layer, a silicon oxynitride layer, a silicon oxide layer, a titanium oxide layer, and an aluminum oxide layer are alternately stacked.

A light blocking layer BML may be disposed on the substrate SUB. The light blocking layer BML may be disposed to overlap an active layer ACT of the thin film transistor TFT to prevent a leakage current occurring when light is incident on the active layer ACT of the thin film transistor TFT. The light blocking layer BML may be covered by the first buffer layer BF1. For example, the light blocking layer BML may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The thin film transistor layer TFTL includes the active layer ACT, a first gate layer GTL1, a second gate layer GTL2, a first source metal layer DTL1, a second source metal layer DTL2, a gate insulating layer 130, a first interlayer insulating layer 141, a second interlayer insulating layer 142, a first planarization layer 160, and a second planarization layer 180.

In one exemplary embodiment, the active layer ACT, a source electrode S, and a drain electrode D may be formed on the first buffer layer BF1. The active layer ACT may include, for example, polycrystalline silicon, monocrystalline silicon, low-temperature polycrystalline silicon, amorphous silicon, or an oxide semiconductor. When the active layer ACT is formed of polycrystalline silicon, the active layer ACT may have conductivity by ion doping. Therefore, the source electrode S and the drain electrode D may be formed by doping ions into active layers ACT.

The gate insulating layer 130 may be formed on the active layer ACT, the source electrode S, and the drain electrode D. The gate insulating layer 130 may be formed of an inorganic layer, for example, a silicon nitride layer, a silicon oxynitride layer, a silicon oxide layer, a titanium oxide layer, or an aluminum oxide layer.

A gate electrode G and a first capacitor electrode CE1 may be formed on the gate insulating layer 130. The gate electrode G and the first capacitor electrode CE1 may be formed as a single layer or multiple layers made of any one of, for example, molybdenum (Mo), aluminum (Al), chromium (Cr), gold (Au), titanium (Ti), nickel (Ni), neodymium (Nd) and copper (Cu) or an alloy thereof.

The first interlayer insulating layer 141 may be formed on the gate electrode G and the first capacitor electrode CE1. The first interlayer insulating layer 141 may be formed of an inorganic layer, for example, a silicon nitride layer, a silicon oxynitride layer, a silicon oxide layer, and a titanium oxide layer, or an aluminum oxide layer. The first interlayer insulating layer 141 may include a plurality of inorganic layers.

A second capacitor electrode CE2 may be formed on the first interlayer insulating layer 141. The second capacitor electrode CE2 may be formed as a single layer or multiple layers made of any one of, for example, molybdenum (Mo), aluminum (Al), chromium (Cr), gold (Au), titanium (Ti), nickel (Ni), neodymium (Nd) and copper (Cu) or an alloy thereof.

The second interlayer insulating layer 142 may be formed on the second capacitor electrode CE2. The second interlayer insulating layer 142 may be formed of, for example, an inorganic layer, for example, a silicon nitride layer, a silicon oxynitride layer, a silicon oxide layer, a titanium oxide layer, or an aluminum oxide layer. The second interlayer insulating layer 142 may include a plurality of inorganic layers.

A first anode connection electrode ANDE1 may be formed on the second interlayer insulating layer 142. The first anode connection electrode ANDE1 may be connected to the source electrode S through a contact hole penetrating the gate insulating layer 130, the first interlayer insulating layer 141, and the second interlayer insulating layer 142. The first anode connection electrode ANDE1 may be formed as a single layer or multiple layers made of any one of, for example, molybdenum (Mo), aluminum (Al), chromium (Cr), gold (Au), titanium (Ti), nickel (Ni), neodymium (Nd) and copper (Cu), or an alloy thereof.

The first planarization layer 160 may be formed on the first anode connection electrode ANDE1 to flatten steps formed due to the active layer ACT, the source electrode S, the drain electrode D, the gate electrode G, the first capacitor electrode CE1, the second capacitor electrode CE2 and the first anode connection electrode ANDE1. The first planarization layer 160 may be formed of an organic layer such as acryl resin, epoxy resin, phenolic resin, polyamide resin, polyimide resin, and the like.

A protective layer 150 may be additionally formed between the first anode connection electrode ANDE1 and the first planarization layer 160. The protective layer 150 may be formed of an inorganic layer, for example, a silicon nitride layer, a silicon oxynitride layer, a silicon oxide layer, a titanium oxide layer, or an aluminum oxide layer.

A second anode connection electrode ANDE2 may be formed on the first planarization layer 160. The second anode connection electrode ANDE2 may be connected to the first anode connection electrode ANDE1 through a contact hole penetrating the first planarization layer 160. The second anode connection electrode ANDE2 may be formed as a single layer or multiple layers made of any one of, for example, molybdenum (Mo), aluminum (Al), chromium (Cr), gold (Au), titanium (Ti), nickel (Ni), neodymium (Nd) and copper (Cu), or an alloy thereof.

The second planarization layer 180 may be formed on the second anode connection electrode ANDE2. The second planarization layer 180 may be formed of an organic layer such as acryl resin, epoxy resin, phenolic resin, polyamide resin, polyimide resin, and the like.

Although FIG. 8 exemplarily illustrates that the thin film transistor TFT is configured to be of a top gate type in which the gate electrode G is located on top of the active layer ACT, it should be noted that the present disclosure is not necessarily limited thereto. That is, the thin film transistor TFT may be configured to be of a bottom gate type in which the gate electrode G is located under the active layer ACT or a double gate type in which the gate electrode G is located on and under the active layer ACT.

The light emitting component layer EML is formed on the thin film transistor layer TFTL. The light emitting component layer EML includes light emitting components 170 and a bank 190.

The light emitting components 170 and the bank 190 are formed on the planarization layer 180. Each of the light emitting components 170 may include a first light emitting electrode 171, the light emitting layer 172, and a second light emitting electrode 173.

The first light emitting electrode 171 may be formed on the second planarization layer 180. The first light emitting electrode 171 may be connected to the second anode connection electrode ANDE2 through a contact hole penetrating the second planarization layer 180.

In a top emission structure in which light is emitted toward the second light emitting electrode 173 when viewed with respect to the light emitting layer 172, the first light emitting electrode 171 may be formed of a metal material having high reflectivity to have a stacked structure (Ti/Al/Ti) of aluminum and titanium, a stacked structure (ITO/Al/ITO) of aluminum and ITO, an APC alloy, and a stacked structure (ITO/APC/ITO) of an APC alloy and ITO. The APC alloy is an alloy of silver (Ag), palladium (Pd), and copper (Cu).

The bank 190 may be formed on the second planarization layer 180 to partition the first light emitting electrode 171, thereby defining an emission area EMA. The bank 190 may be formed to cover the edge of the first light emitting electrode 171. The bank 190 may be formed of an organic layer such as acryl resin, epoxy resin, phenolic resin, polyamide resin, polyimide resin, and the like.

The emission area EMA represents an area in which the first light emitting electrode 171, the light emitting layer 172, and the second light emitting electrode 173 are sequentially stacked, and holes from the first light emitting electrode 171 and electrons from the second light emitting electrode 173 are combined in the light emitting layer 172 to emit light.

The light emitting layer 172 is formed on the first light emitting electrode 171 and the bank 190. The light emitting layer 172 may include an organic material. The organic material may be configured to emit light in a predetermined color. For example, the light emitting layer 172 may include a hole transporting layer, an organic material layer, and an electron transporting layer.

The second light emitting electrode 173 is formed on the light emitting layer 172. The second light emitting electrode 173 may be formed to cover the light emitting layer 172. The second light emitting electrode 173 may be a common layer which is commonly formed in sub-pixels SP1, SP2, and SP3. A capping layer may be formed on the second light emitting electrode 173.

In the top emission type structure, the second light emitting electrode 173 may be formed of a transparent conductive material (TCO) such as ITO or IZO capable of transmitting light or a semi-transmissive conductive material such as magnesium (Mg), silver (Ag), or an alloy of magnesium (Mg) and silver (Ag). When the second light emitting electrode 173 is formed of a semi-transmissive conductive material, the light emission efficiency can be increased due to a micro-cavity effect.

The encapsulation layer TFE may be formed on the light emitting component layer EML.

The encapsulation layer TFE may include at least one inorganic layer to prevent oxygen or moisture from permeating into the light emitting component layer EML. In addition, the encapsulation layer TFE may include at least one organic layer to protect the light emitting component layer EML from foreign substances such as dust. For example, the encapsulation layer TFE may include a first inorganic layer TFE1, an organic layer TFE2, and a second inorganic layer TFE3.

In one exemplary embodiment, the first inorganic layer TFE1, the organic layer TFE2, and the second inorganic layer TFE3 may be sequentially disposed on the second light emitting electrode 173 in that order. The first inorganic layer TFE1 and the second inorganic layer TFE3 may be formed of multiple layers in which one or more inorganic layers of, for example, a silicon nitride layer, a silicon oxynitride layer, a silicon oxide layer, a titanium oxide layer, and an aluminum oxide layer are alternately stacked. The organic layer TFE2 may be a monomer.

The touch electrode layer SENL is disposed on the encapsulation layer TFE. The touch electrode layer SENL includes, for example, a second buffer layer BF2, touch electrodes SE, and a first touch insulating layer TINS1.

The second buffer layer BF2 may be disposed on the encapsulation layer TFE. The second buffer layer BF2 may include at least one inorganic layer. For example, the second buffer layer BF2 may be formed of multiple layers in which one or more inorganic layers of, for example, a silicon nitride layer, a silicon oxynitride layer, a silicon oxide layer, a titanium oxide layer, and an aluminum oxide layer are alternately stacked. The second buffer layer BF2 may be omitted.

The first touch insulating layer TINS1 may be disposed on the second buffer layer BF2. The first touch insulating layer TINS1 may be formed of an inorganic layer, for example, a silicon nitride layer, a silicon oxynitride layer, a silicon oxide layer, and a titanium oxide layer, or an aluminum oxide layer. Alternatively, the first touch insulating layer TINS1 may be formed of an organic layer such as acryl resin, epoxy resin, phenolic resin, polyamide resin, polyimide resin and the like.

The touch electrodes SE may be disposed on the first touch insulating layer TINS1. The touch electrodes SE do not overlap the emission area EMA. That is, the touch electrodes SE are not disposed in the emission area EMA. The touch electrodes SE may be formed of a single layer containing, for example, molybdenum (Mo), titanium (Ti), copper (Cu), or aluminum (Al). The touch electrodes SE or may also be formed to have a stacked structure (Ti/Al/Ti) of aluminum and titanium, a stacked structure (ITO/Al/ITO) of aluminum and indium tin oxide (ITO), an Ag—Pd—Cu (APC) alloy, or a stacked structure (ITO/APC/ITO) of APC alloy and ITO.

A second touch insulating layer TINS2 may be disposed on the touch electrodes SE. The second touch insulating layer TINS2 may include at least one of an inorganic layer or an organic layer. The inorganic layer may be, for example, a silicon nitride layer, a silicon oxynitride layer, a silicon oxide layer, a titanium oxide layer, or an aluminum oxide layer. The organic layer may include acryl resin, epoxy resin, phenolic resin, polyamide resin, or polyimide resin.

The cover window 100 may be disposed on the touch electrode layer SENL. A polarizing film and an impact absorbing layer may be additionally disposed between the touch electrode layer SENL and the cover window 100.

in one exemplary embodiment, a dam structure DAM may be disposed at least partially around the through hole TH. The dam structure DAM may include at least one of the insulating layers BF1, 130, 141, 142, 160, 180, and 190 stacked in the thin film transistor layer TFTL and the light emitting component layer EML. A trench TCH from which the insulating layers BF1, 130, 141, 142, 160, 180, and 190 are removed may be disposed between the dam structure DAM and the emission area EMA. At least a portion of the encapsulation layer TFE may be disposed in the trench TCH. For example, the organic layer TFE2 of the encapsulation layer TFE may be disposed up to the dam structure DAM. For example, the organic layer TFE2 of the encapsulation layer TFE may not be disposed between the dam structure DAM and the through hole TH. A first organic layer 228 can be prevented from overflowing into the through hole TH by the dam structure DAM. FIG. 8 illustrates that the first inorganic layer TFE1 and the second inorganic layer TFE3 end on the dam structure DAM, but the present disclosure is not necessarily limited thereto. For example, the first inorganic layer TFE1 and the second inorganic layer TFE3 may end in an area between the dam structure DAM and the through hole TH.

A light blocking pattern 230 may be disposed on one surface of the cover window 100. The light blocking pattern 230 may overlap the dam structure DAM in the third direction (Z-axis direction). The light blocking pattern 230 may overlap the edge of the through hole TH in the third direction (Z-axis direction).

At least one of organic layers 228 and 229 may be further disposed on the encapsulation layer TFE in the area between the dam structure DAM and the through hole TH. For example, the first organic layer 228 may be disposed on the second inorganic layer TFE3, and a second organic layer 229 may be disposed on the first organic layer 228. For example, the first organic layer 228 and the second organic layer 229 may serve to fill the space between the dam structure DAM and the through hole TH to perform the planarization.

Figure 9:
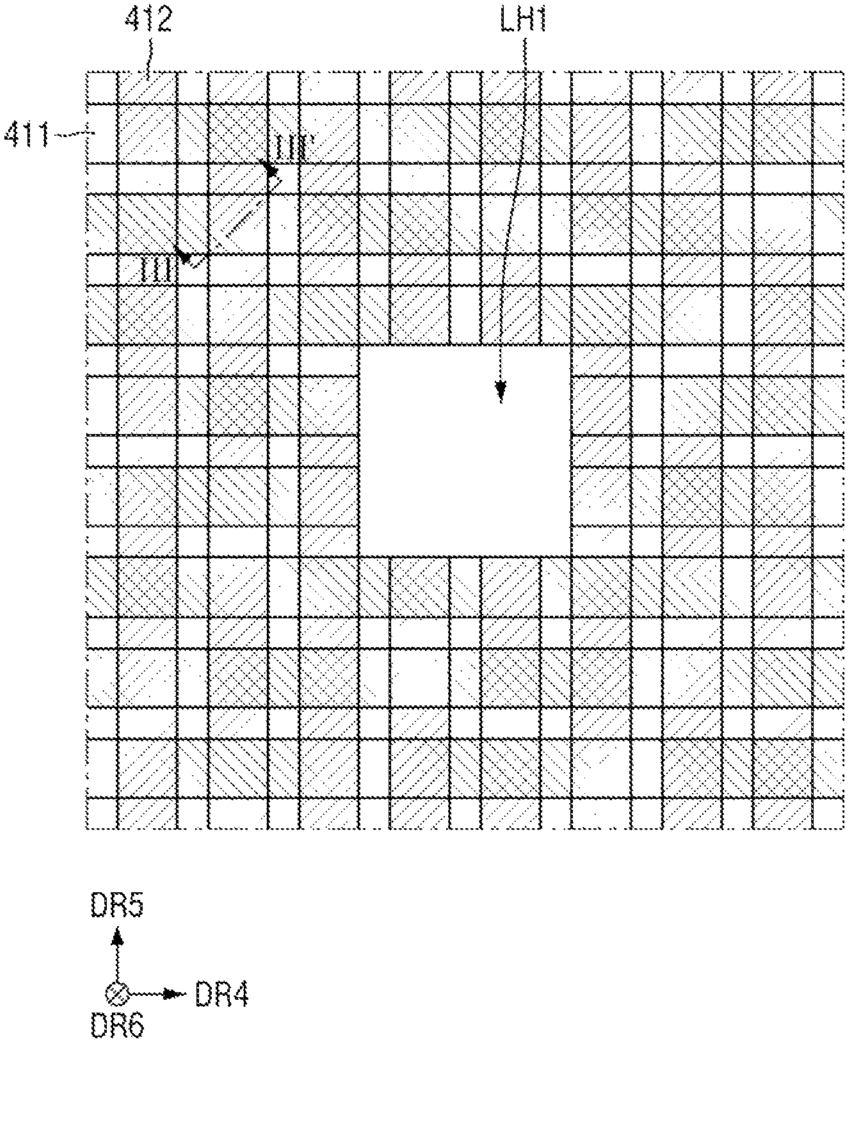
FIG. 9 is a layout view showing force sensor electrodes and a first optical hole of a force sensor according to one exemplary embodiment.
Figure 10:
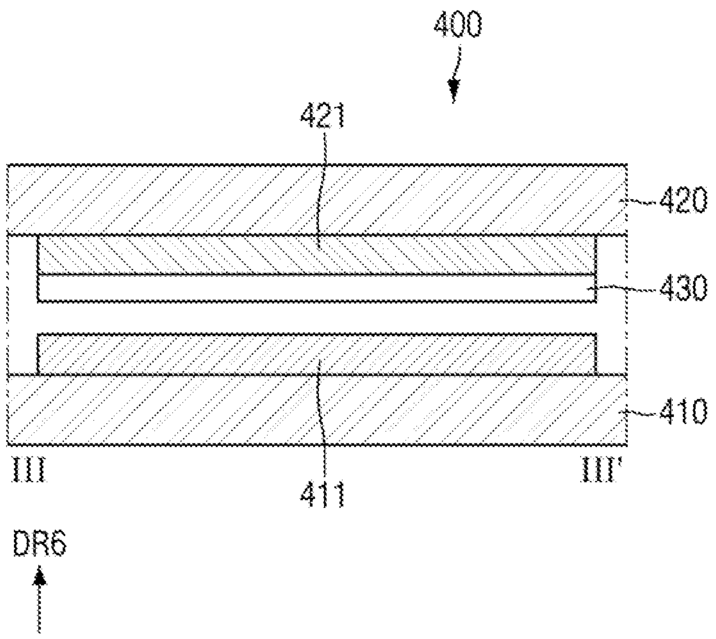
FIG. 10 is a cross-sectional view showing an example of the force sensor of FIG. 8.

FIG. 9 is a layout view showing force sensor electrodes and a first optical hole of a force sensor according to one exemplary embodiment. FIG. 10 is a cross-sectional view showing an example of the force sensor of FIG. 8.

Referring to FIGS. 9 and 10, the force sensor 400 may include a first base substrate 410, a first force sensor electrode 411, a second base substrate 420, a second force sensor electrode 421, and a force sensing layer 430 disposed between the first force sensor electrode 411 and the second force sensor electrode 421.

Each of the first base substrate 410 and the second base substrate 420 may include polyethylene, polyimide, polycarbonate, polysulfone, polyacrylate, polystyrene, polyvinyl chloride, polyvinyl alcohol, polynorbornene, or polyester-based material. In one exemplary embodiment, each of the first base substrate 410 and the second base substrate 420 may be made of a polyethylene terephthalate (PET) film or a polyimide film.

The first base substrate 410 and the second base substrate 420 may be bonded to each other via a bonding layer. The bonding layer may include an adhesive material. The bonding layer may be disposed along the edges of the first base substrate 410 and the second base substrate 420, but the present disclosure is not necessarily limited thereto.

The first force sensor electrodes 411 may be disposed on one surface of the first base substrate 410, which faces the second base substrate 420. The second force sensor electrodes 421 may be disposed on one surface of the second base substrate 420, which faces the first base substrate 410. Each of the first force sensor electrode 411 and the second force sensor electrode 421 may include a conductive material. For example, each of the first force sensor electrode 411 and the second force sensor electrode 421 may be made of a metal such as silver (Ag) or copper (Cu), a transparent conductive oxide such as ITO, IZO, or ZIO, carbon nanotubes, conductive polymers, or the like. One of the first force sensor electrode 411 and the second force sensor electrode 421 may be a force driving electrode, and the other may be a force sensing electrode.

Figure 11:
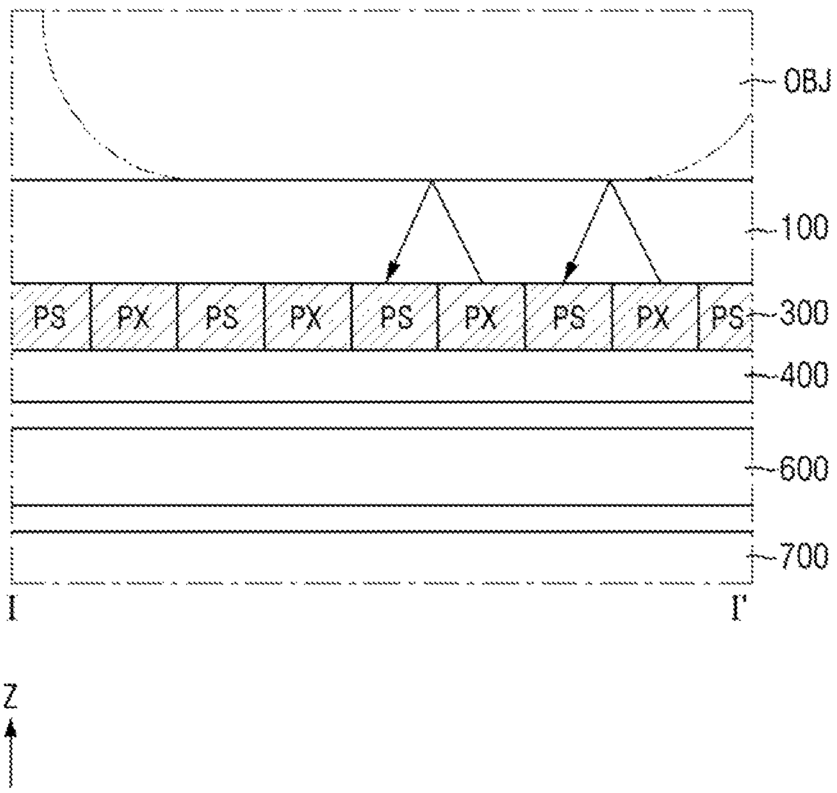
FIG. 11 is a cross-sectional view showing structures of a cover window, a display panel, a force sensor, a light emitting member, a light receiving sensor, and the like taken along lines I-I' of FIG. 4.

The force sensing layer 430 may be disposed between the first force sensor electrode 411 and the second force sensor electrode 421. The force sensing layer 430 may be in contact with at least one of the first force sensor electrode 411 or the second force sensor electrode 421. For example, the force sensing layer 430 may be in contact with the second force sensor electrode 421 as shown in FIG. 10 or may be in contact with the first force sensor electrode 411 as shown in FIG. 11.

The force sensing layer 430 may include a force sensitive material. The force sensitive material may contain metal nanoparticles formed of, for example, nickel, aluminum, tin, copper and the like, or carbon. The force sensitive material may be provided in polymer resin in the form of particles, but the present disclosure is not necessarily limited thereto.

When a force is applied to the force sensor 400, the first force sensor electrode 411, the force sensing layer 430, and the second force sensor electrode 421 may be electrically connected. According to the force applied to the force sensor 400, the electrical resistance of the force sensing layer 430 may become lower. In some cases, the electrical resistance of the force sensing layer 430 may be calculated by applying a force driving voltage to the first force sensor electrode 411 and measuring a force sensing voltage through the second force sensor electrode 421. According to the electrical resistance of the force sensing layer 430, it is possible to determine whether a force has been applied or not and calculate the magnitude of the force.

The first force sensor electrodes 411 may extend in a fourth direction DR4 and may be arranged in a fifth direction DR5. The second force sensor electrodes 421 may extend in the fifth direction DR5 and may be arranged in the fourth direction DR4. The first force sensor electrodes 411 and the second force sensor electrodes 421 may cross each other. For example, crossing regions of the first force sensor electrodes 411 and the second force sensor electrodes 421 may be arranged in a matrix fashion. A crossing region of the first force sensor electrodes 411 and the second force sensor electrodes 421 may be a force sensing cell for sensing a force. For example, a force may be sensed in each of the crossing regions of the first force sensor electrodes 411 and the second force sensor electrodes 421.

According to one exemplary embodiment, when the first force sensor electrode 411 and the second force sensor electrode 421 include an opaque conductive material or the force sensing layer 430 includes an opaque polymer resin, the force sensor 400 may be opaque. The force sensor 400 may include the first optical hole LH1 To prevent light. Among the first force sensor electrode 411, the second force sensor electrode 421, and the force sensing layer 430, a component including an opaque material may be removed from the first optical hole LH1. For example, when the first force sensor electrode 411 and the second force sensor electrode 421 include an opaque conductive material, the first force sensor electrode 411 and the second force sensor electrode 421 may be removed from the first optical hole LH1. According to one exemplary embodiment, when the force sensing layer 430 includes an opaque polymer resin, the force sensing layer 430 may be removed from the first optical hole LH1. When the first force sensor electrode 411 and the second force sensor electrode 421 include an opaque conductive material and the force sensing layer 430 includes an opaque polymer resin, the first force sensor electrode 411, the second force sensor electrode 421, and the force sensing layer 430 may be removed from the first optical hole LH1.

According to some exemplary embodiments, alternatively, the first base substrate 410 and the second base substrate 420 may include the first force sensor electrode 411, the second force sensor electrode 421, and the force sensing layer 430. For example, the first base substrate 410 may include the first force sensor electrode 411 and the force sensing layer 430, and the second base substrate 420 may include the second force sensor electrode 421. Alternatively, any one of the first base substrate 410 and the second base substrate 420 may include the first force sensor electrode 411, the second force sensor electrode 421, and the force sensing layer 430.

FIG. 9 illustrates eight first-force sensor electrodes 411 and eight second-force sensor electrodes 421 for simplicity of description, but the numbers of the first force sensor electrodes 411 and the second force sensor electrodes 421 are not necessarily limited thereto. The lengths of the force sensor 400 in the fourth direction DR4 and in the fifth direction DR5 may be in a range of about 10 mm to 20 mm. The lengths of the crossing region of the first force sensor electrode 411 and the second force sensor electrode 421 in the fourth direction DR4 and the fifth direction DR5 may be about 1.5 mm or more. The lengths of the first optical hole LH1 in the fourth direction DR4 and in the fifth direction DR5 may be about 3 mm or more.

FIG. 11 is a cross-sectional view of another embodiment showing structures of a cover window, a display panel, a force sensor, a light emitting member, a light receiving sensor, and the like taken along line I-I' of FIG. 4. The lower cover 900 is not illustrated in FIG. 11 for simplicity of description.

Referring to FIG. 11, the display device 10 may include the display panel 300, the force sensor 400, the bracket 600, and the main circuit board 700. In the display panel 300, a light sensing pixel PS including the light receiving sensor 740 is disposed between the image display pixels PX. Accordingly, the light receiving sensor 740 may be disposed in the through hole TH toward the front side of the display panel 300, or disposed between the pixels PX to sense light reflected toward the display panel 300.

Figure 12:
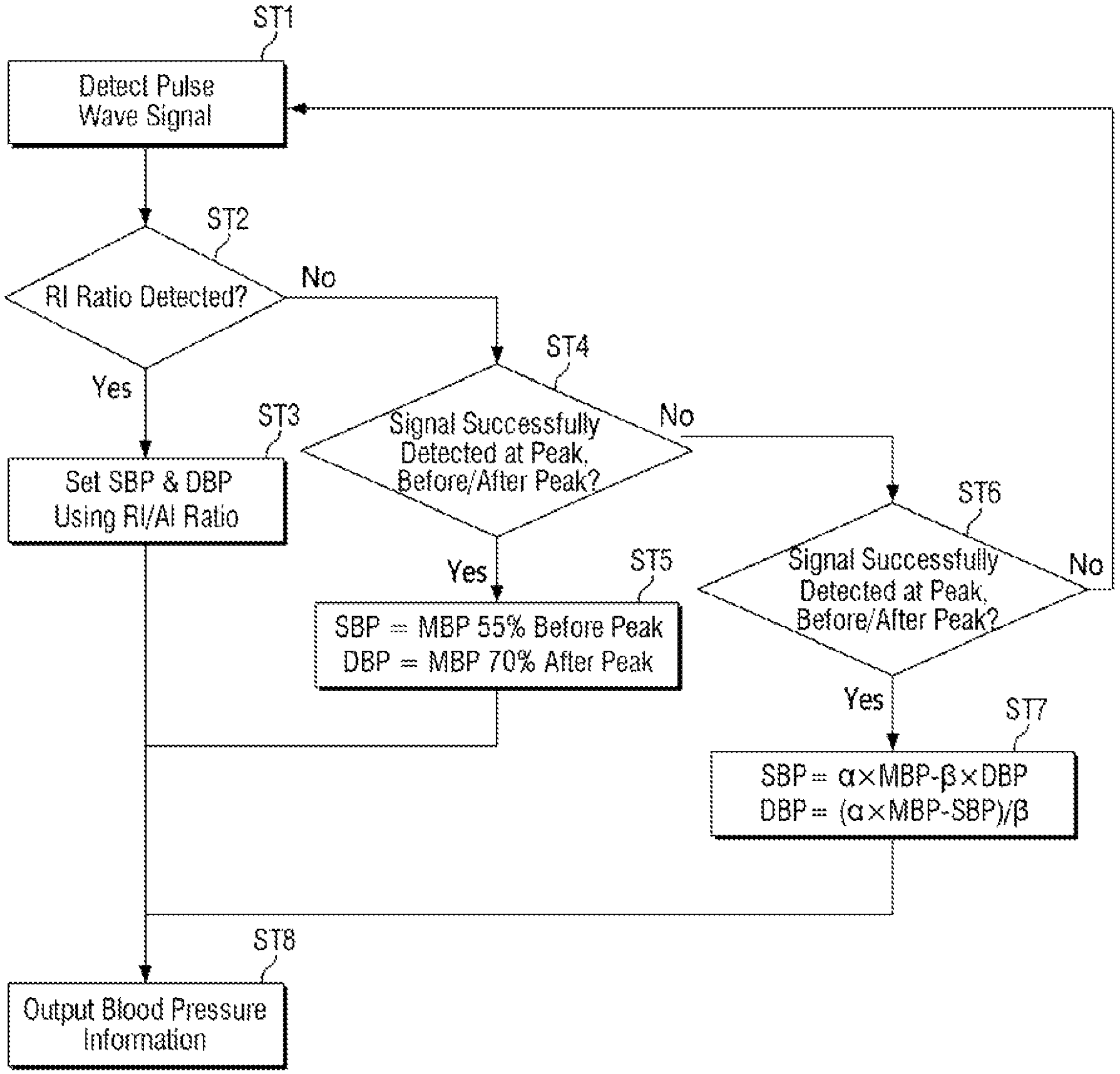
FIG. 12 is a flowchart illustrating a blood pressure measurement process by the main processor shown in FIG. 2.
Figure 13:
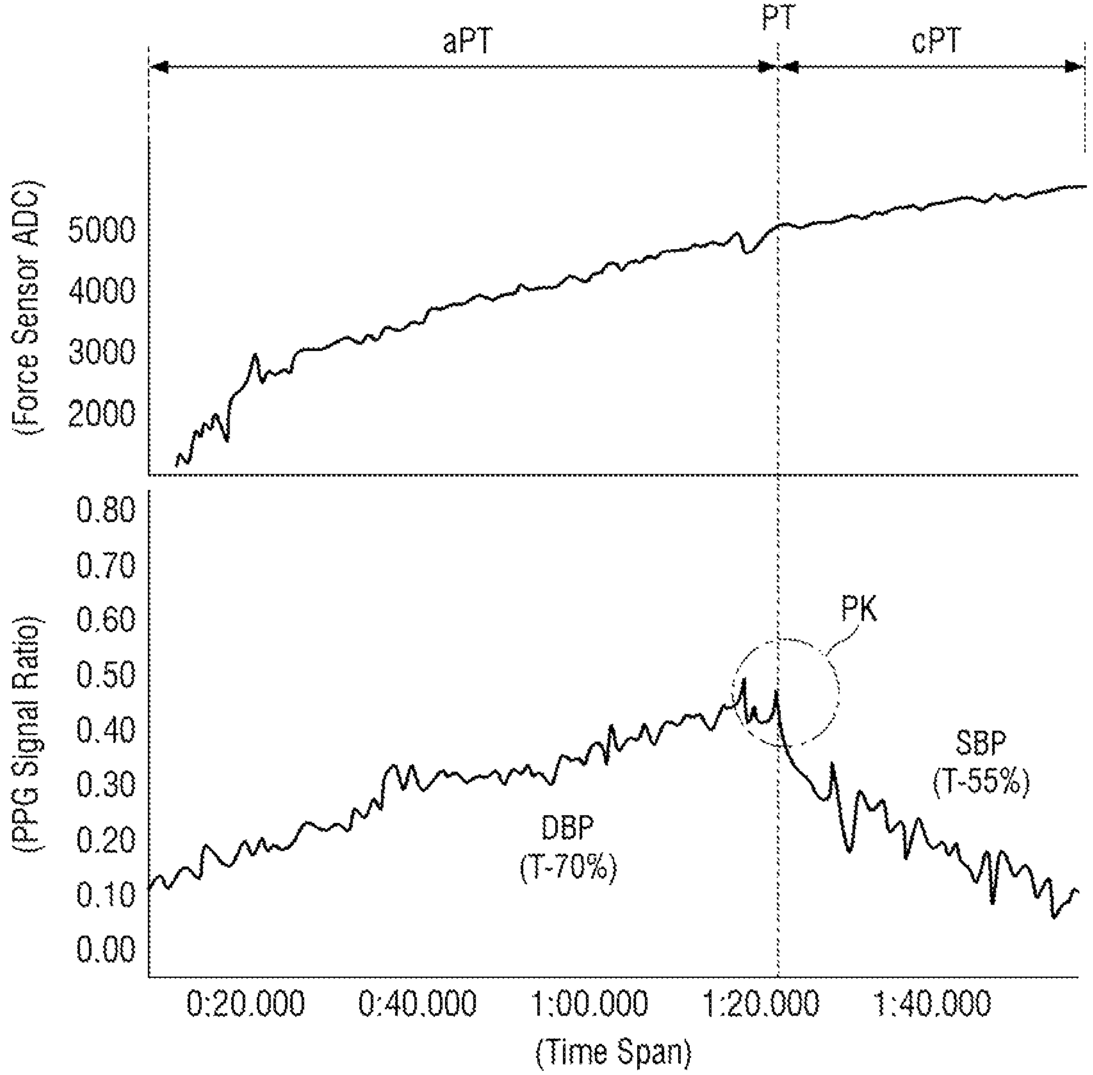
FIG. 13 is a graph illustrating a blood pressure calculation method by the main processor according to one exemplary embodiment.

FIG. 12 is a flowchart illustrating a blood pressure measurement process by the main processor shown in FIG. 2. FIG. 13 is a graph for explaining a blood pressure calculation method by the main processor according to one exemplary embodiment.

Referring to FIG. 13 in conjunction with FIG. 12, step ST1 of detecting a reflected pulse wave value ratio (RI ratio) and step ST2 of measuring a blood pressure using the reflected pulse wave value ratio (RI ratio) will be described as follows.

First, in ST1, when a force value (force sensor ADC) is calculated by the force sensor 400, the main processor 710 detects a benchmark that can be used to measure a blood pressure. For example, the benchmark can be a reflected pulse wave value ratio (RI). In this example, a pulse wave signal (PPG signal ratio) is generated according to the amount of light sensed by the light receiving sensor 740 and an optical signal corresponding to the amount of light. Then, in ST2, the reflected pulse wave value and the reflected pulse wave value ratio (RI ratio) are detected from the pulse wave signal detected in real time.

The reflected pulse wave value ratio (RI ratio) may be a ratio of the reflected pulse wave value, which rises corresponding to a reflected wave of a blood vessel, to a highest pulse wave value corresponding to a heartbeat, in the pulse wave signal detected in real time.

Figure 14:
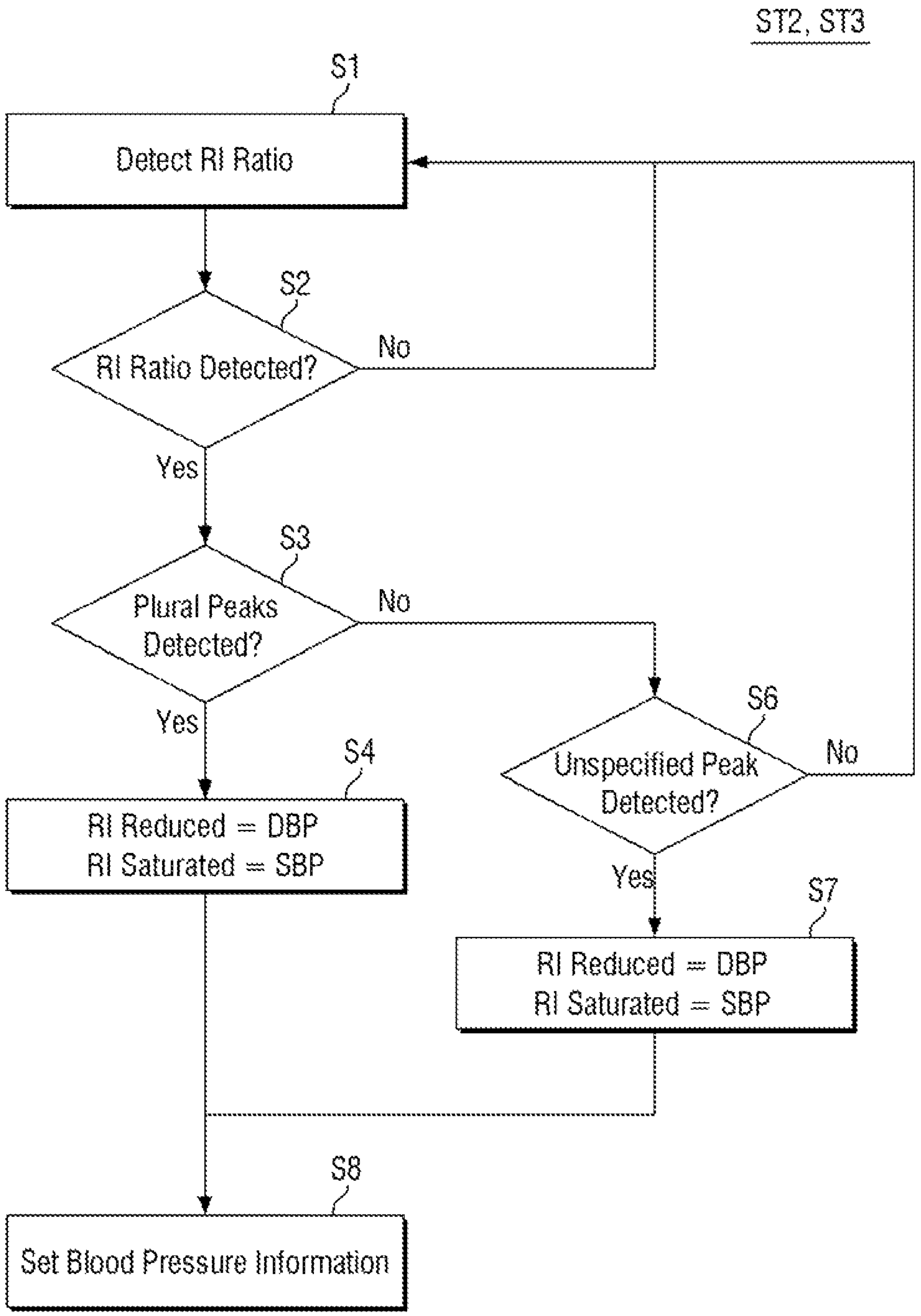
FIG. 14 is a flowchart illustrating a process of detecting a reflected pulse wave value ratio (RI ratio) and a process of measuring a blood pressure using the reflected pulse wave value ratio (RI ratio) of FIG. 12.
Figure 15A:
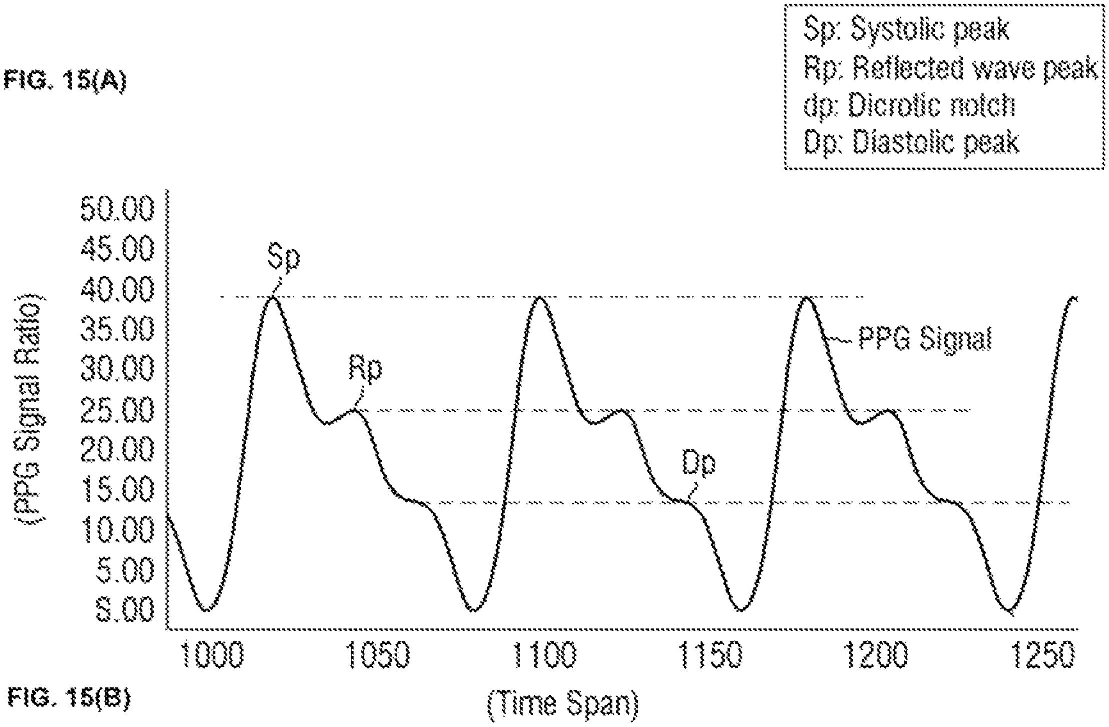
FIGS. 15A and 15B are enlarged graphs more specifically showing a detected waveform of the pulse wave signal illustrated in FIG. 13.
Figure 15B:
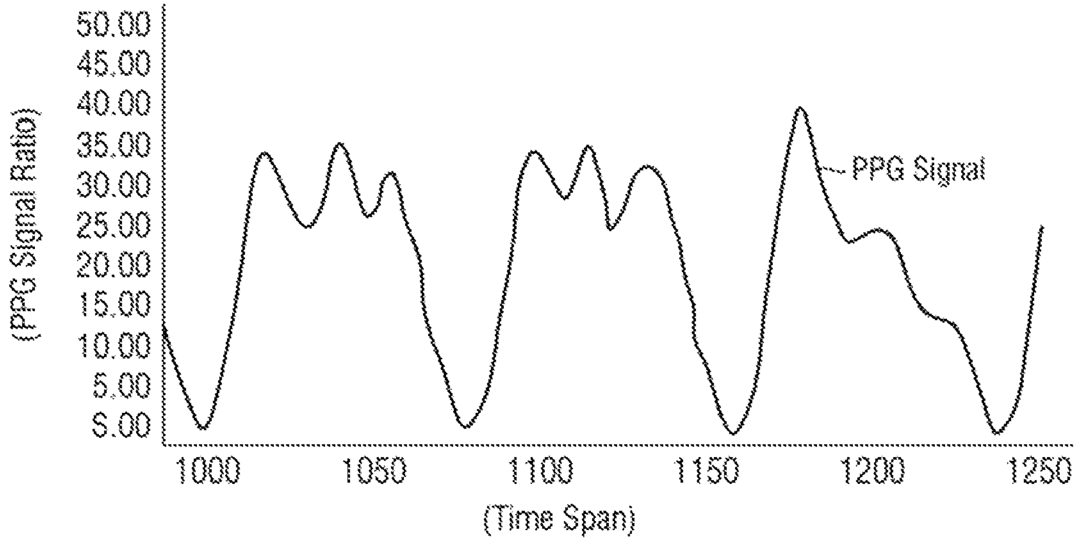
Figure 16:
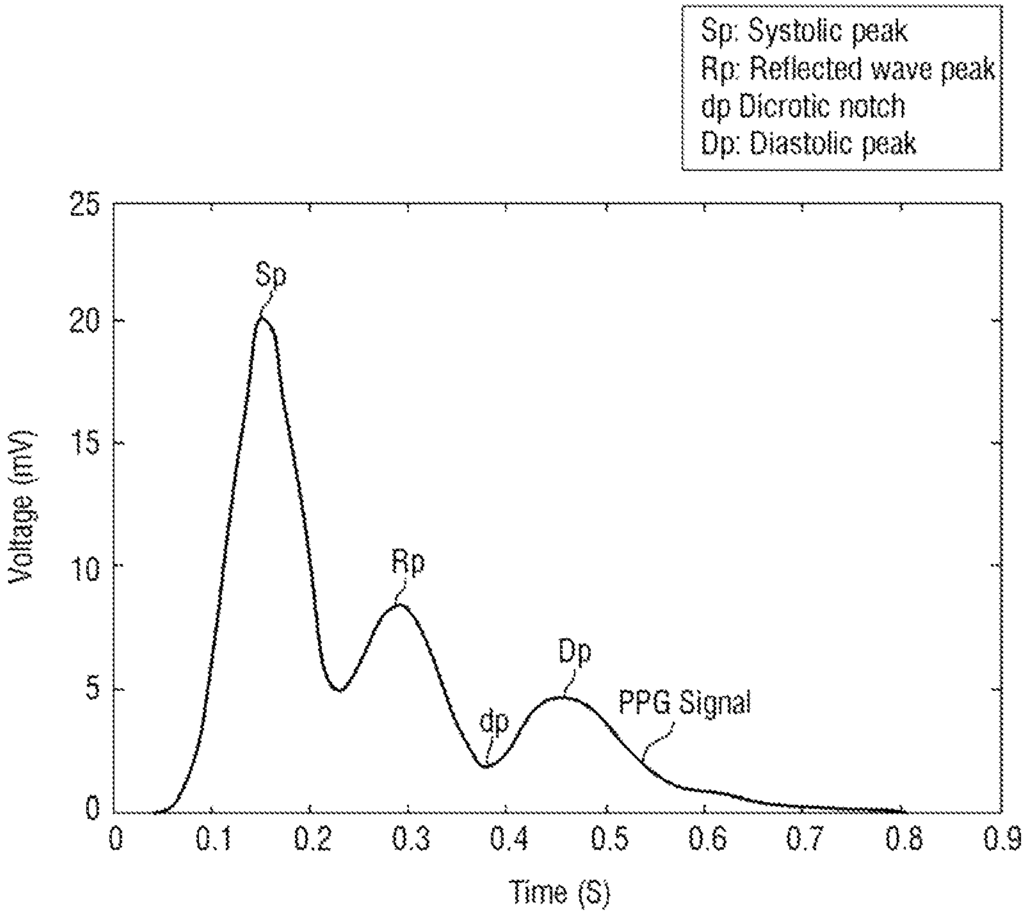
FIG. 16 is a graph for explaining a method of detecting a highest pulse wave value, a reflected pulse wave value, and a reflected pulse wave value ratio (RI ratio) with respect to the pulse wave signal shown in FIGS. 15A and 15B.

FIG. 14 is a flowchart illustrating a process of detecting a reflected pulse wave value ratio (RI ratio) and a process of measuring a blood pressure using the reflected pulse wave value ratio (RI ratio) of FIG. 12. FIGS. 15A and 15B are enlarged graphs more specifically showing a detected waveform of the pulse wave signal illustrated in FIG. 13. FIG. 16 is a graph for explaining a method of detecting a highest pulse wave value, a reflected pulse wave value, and a reflected pulse wave value ratio (RI ratio) with respect to the pulse wave signal shown in FIGS. 15A and 15B.

Referring to FIGS. 15A and 16, in order to detect the reflected pulse wave value ratio (RI ratio), the main processor 710 divides a wave period of a pulse wave signal generated in real time according to a period in which a wave corresponding to a heartbeat and a reflected wave of a blood vessel sequentially occur. For example, one period of the pulse wave signal may include a highest pulse wave value Sp corresponding to a heartbeat, a reflected pulse wave value Rp that rises corresponding to a reflected wave of a blood vessel, a lowest pulse wave value Dp in a lowered state until the next heartbeat, and a rebound pulse wave value dp corresponding to a heartbeat. Accordingly, the main processor 710 may set the period of the pulse wave signal as a wave period in which the highest pulse wave value Sp, the reflected pulse wave value Rp, the lowest pulse wave value Dp, and the rebound pulse wave value dp sequentially occur.

The main processor 710 may detect the highest pulse wave value Sp corresponding to a heartbeat and the reflected pulse wave value Rp corresponding to a reflected wave during each divided period of the pulse wave signal. In step S1, the main processor 710 may detect the ratio (RI ratio) of the reflected pulse wave value to the highest pulse wave value during each period of the pulse wave signal using Eq. 1 below.

$$RI\ \text{ratio}=Rp/Sp \quad \text{(Eq. 1)}$$

Here, Sp is the highest pulse wave value during each period of the pulse wave signal, and Rp is the reflected pulse wave value detected after the highest pulse wave value.

FIG. 15B shows an example in which the highest pulse wave value Sp and the reflected pulse wave value Rp are inaccurately detected within one period of the pulse wave signal. As shown in FIG. 15B, when the highest pulse wave value Sp and the reflected pulse wave value Rp is inaccurately generated, the period of the pulse wave signal may not be set By the main processor 710. Accordingly, the main processor 710 is configured to generate again a pulse wave signal according to the optical signal to detect and set a peak detection value PK and a lowest pulse wave signal value within a predetermined period. Then, in step S2, the ratio (RI ratio) of the reflected pulse wave value to the highest pulse wave value may be detected for each divided period of the pulse wave signal using Eq. 1 on some conditions. For example, the RI ration may be detected when a wave period is identified, wherein the highest pulse wave value Sp, the reflected pulse wave value Rp, the lowest pulse wave value Dp, and the rebound pulse wave value dp sequentially occur In the wave period.

Figure 17:
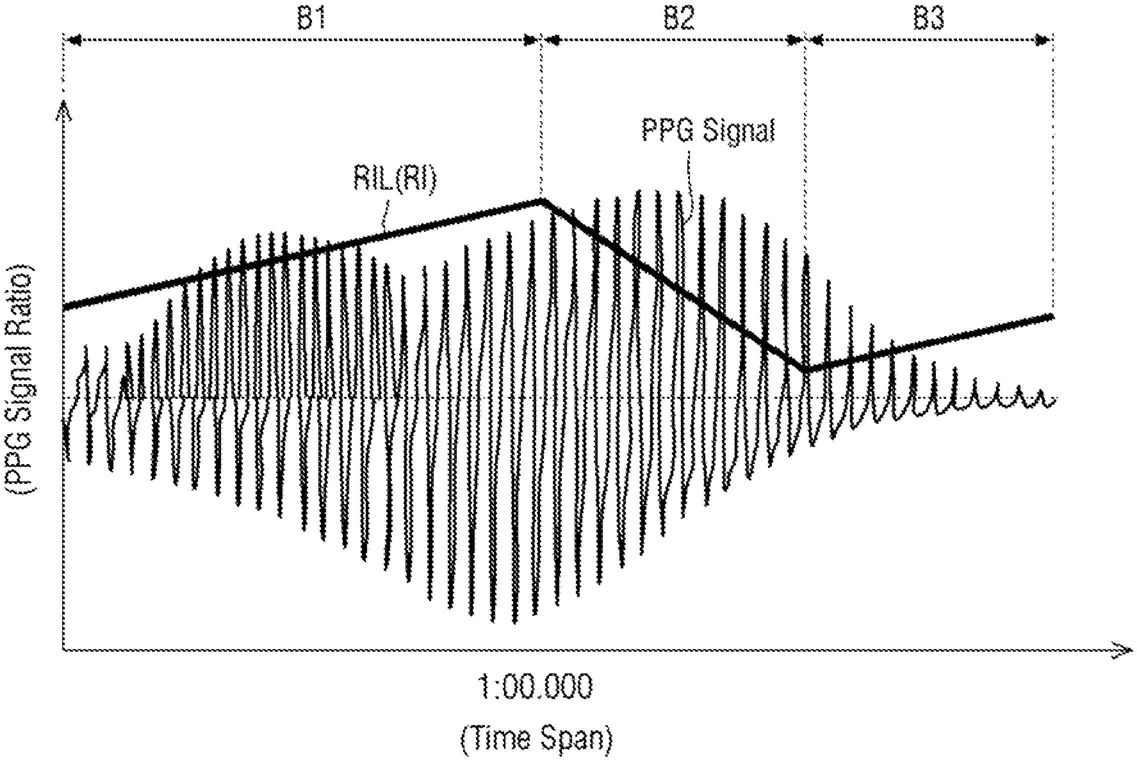
FIG. 17 is a graph illustrating a method of measuring a blood pressure according to detection results of a pulse wave signal and a reflected pulse wave value ratio (RI ratio)

FIG. 17 is a graph for explaining a method of measuring a blood pressure according to detection results of a pulse wave signal and a reflected pulse wave value ratio (RI ratio).

Referring to FIGS. 14 and 17, in step S3, the main processor 710 sequentially stores the detected RI ratio and analyzes the stored RI ratio. In this case, as shown in FIG. 17, the main processor 710 may continuously create data of the change in the pulse wave value ratio (RI ratio) stored during a detection period of the peak detection value PK to analyze a change in the size of pulse wave value ratio data RIL(RI).

The main processor 710 analyzes the pulse wave value ratio data RIL(RI) stored during the detection period of the peak detection value PK to analyze a first period B1 during which the pulse wave value ratio (RI ratio) is in a saturated state to change with little variation within a preset range, a rapid change period B2 during which the pulse wave value ratio (RI ratio) rapidly decreases or increases beyond the preset range in a predetermined period, a second period B3 during which the pulse wave value ratio (RI ratio) is in the saturated state again to change with little variation within the preset range after rapidly decreasing or increasing, and the like.

Figure 18:
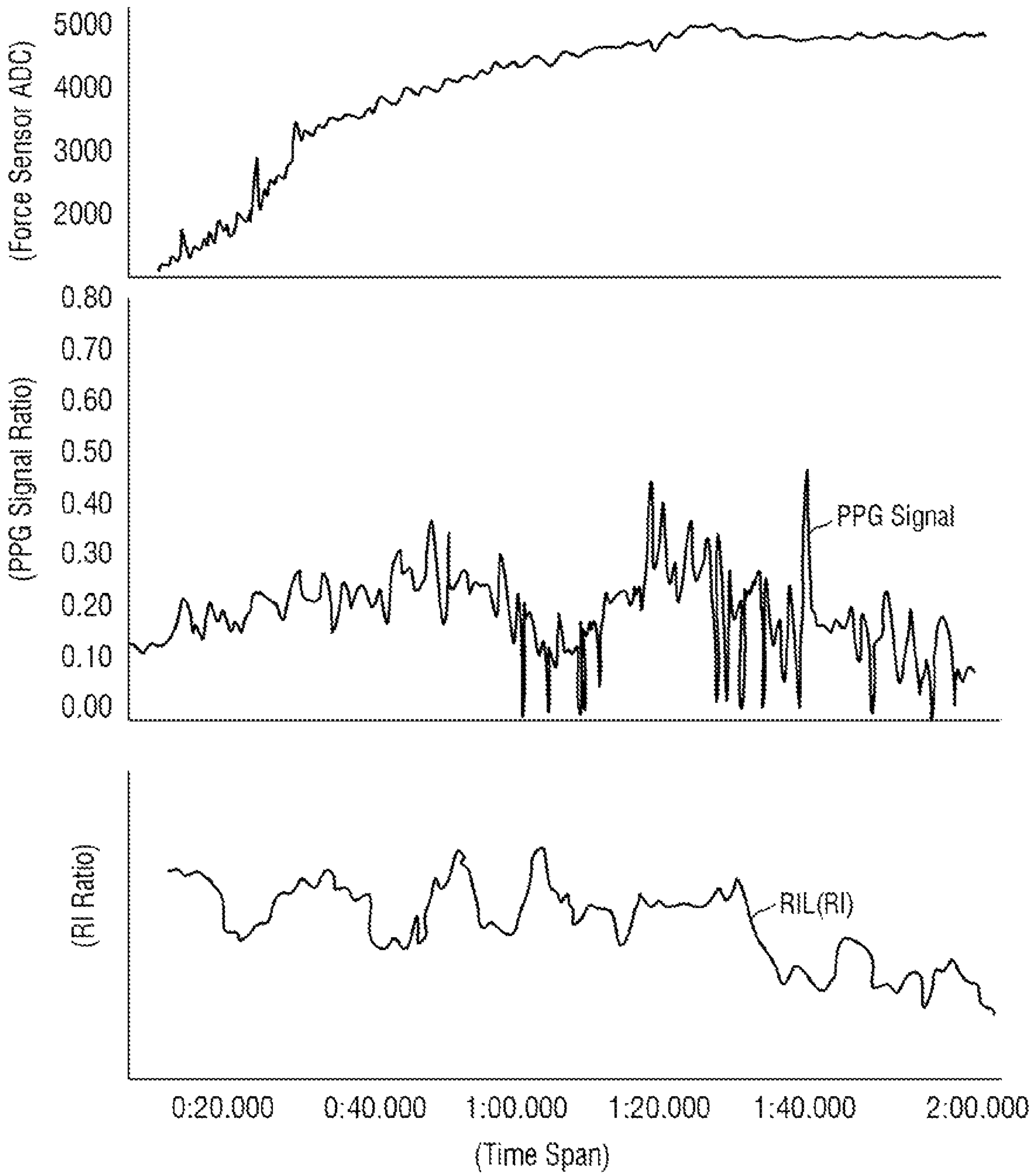
FIG. 18 are graphs demonstrating detection results of a pulse wave signal and a reflected pulse wave value ratio which have been inaccurately varied and detected.

FIG. 18 shows graphs of detection results of a pulse wave signal and a reflected pulse wave value ratio which have been inaccurately varied and detected.

Referring to FIG. 18, the main processor 710 may analyze the pulse wave value ratio data RIL(RI) stored for the detection period of the peak detection value PK. However, the first period B1, during which the pulse wave value ratio (RI ratio) changes with little variation, the rapid change period B2, during which the pulse wave value ratio (RI ratio) rapidly changes, the second period B3, during which the pulse wave value ratio (RI ratio) changes again with little variation, and the like may not be analyzed. That is, when the pulse wave value ratio (RI ratio) is inaccurately detected due to the inaccurate pulse wave signal, it is confirmed that the pulse wave value ratio data RIL(RI) is also inaccurate. As shown in FIG. 18, when the pulse wave value ratio (RI ratio) is inaccurately detected, the main processor 710 generates again a pulse wave signal according to the optical signal and detects the peak detection value PK within a predetermined period to increase the accuracy.

According to one exemplary embodiment, the RI ratio may change within different ranges during different periods. For example, during the first period, B1 and the second period B3, the pulse wave value ratio (RI ratio) changes within a preset range, and during the rapid change period B2, the pulse wave value ratio (RI ratio) changes beyond the preset range. In this case, the main processor 710 may still be configured to calculate blood pressure information even in a period during which the peak detection value PK is detected somewhat inaccurately.

Figure 19:
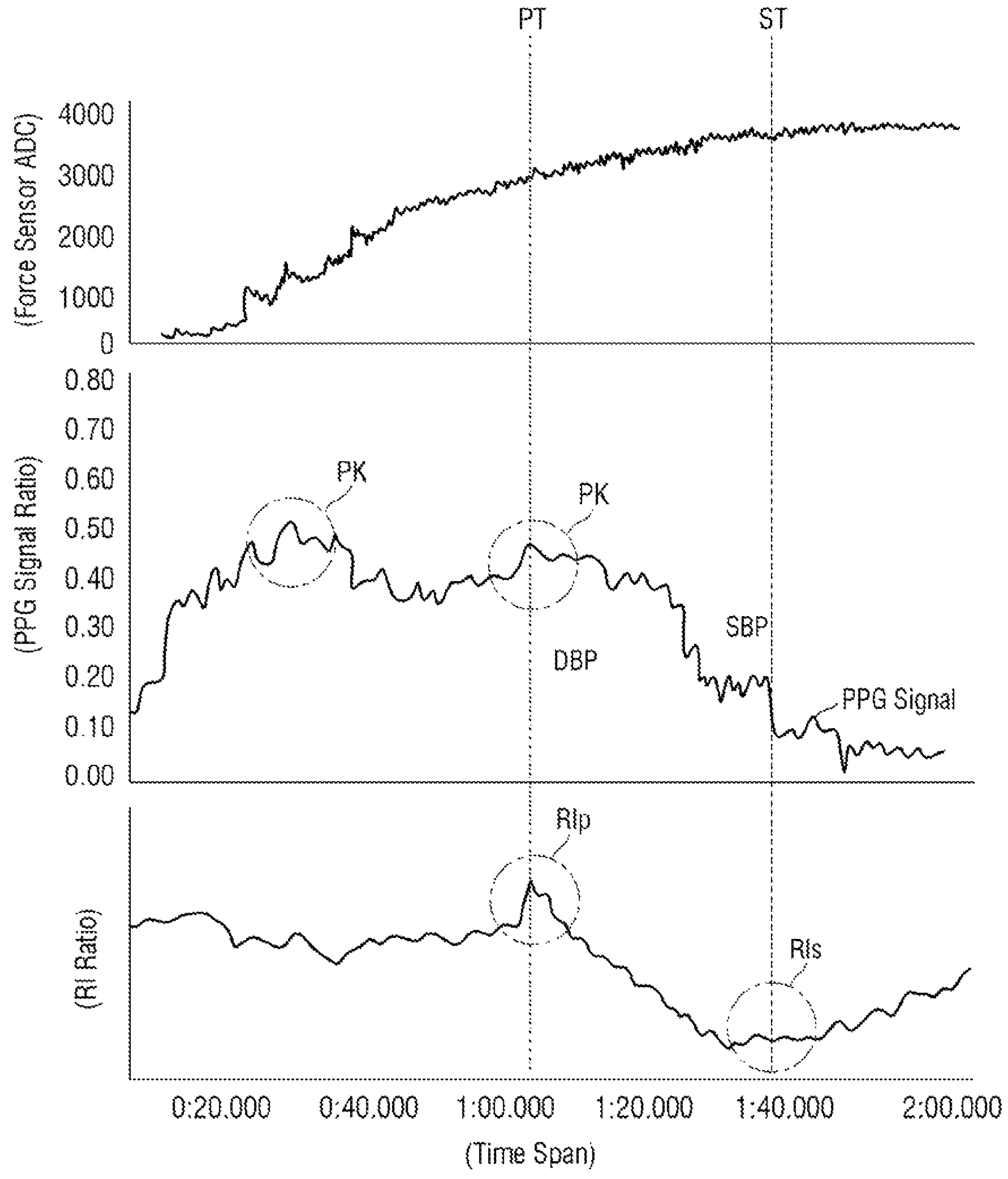
FIG. 19 is a graph illustrating a method of measuring a blood pressure using a detected pulse wave signal and reflected pulse wave value ratio.

FIG. 19 is a graph illustrating a method of measuring a blood pressure using a detected pulse wave signal and reflected pulse wave value ratio.

The main processor 710 may calculate blood pressure information during an unstable detection period. An unstable detection period of the peak detection value PK at least includes a period during which a plurality of peak detection values PK are detected during the detection period of the peak detection value PK, the peak detection values PK having magnitudes within a range. In step S4, the main processor 710 detects blood pressure information including a diastolic blood pressure (DBP) and a systolic blood pressure (SBP) by analyzing the pulse wave value ratio data RIL(RI). In this step, the main processor 710 may continuously create data of the change in the pulse wave value ratios (RI ratios) sequentially generated and stored during the detection period of the peak detection value PK to analyze the change in the size of the pulse wave value ratio data RIL(RI).

According to one exemplary embodiment, the main processor 710 may be configured to detect a start time Rip (or PT) of the rapid change period B2 during which the pulse wave value ratio (RI ratio) rapidly changes. Further, the main processor 710 may set a pulse wave signal detection value at the start time Rip of the rapid change period B2, as the DBP when the heart relaxes. Further, the main processor 710 may detect a start time Ris (or ST) of the second period B3 during which the pulse wave value ratio (RI ratio) changes with little variation, and may set a pulse wave signal detection value at the start time Ris (or ST) of the second period B3, as the SBP when the heart contracts. Further, the main processor 710 may set any one pulse wave signal detection value during a period, during which the pulse wave value ratio (RI ratio) is in the saturated state to change with little variation, as a mean blood pressure (MBP).

Figure 20:
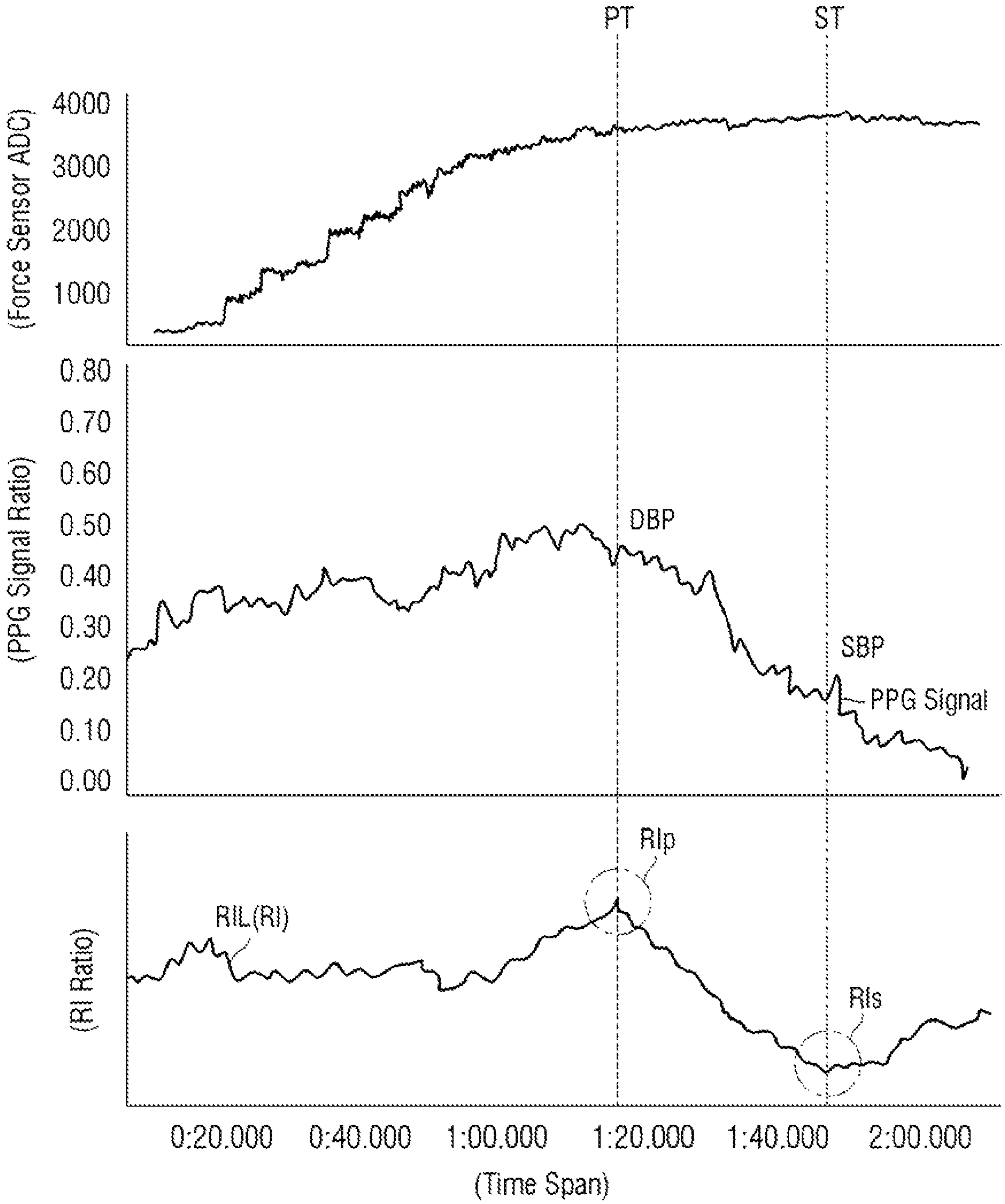
FIG. 20 is another graph showing a method of measuring a blood pressure using a detected pulse wave signal and reflected pulse wave value ratio.

FIG. 20 is another graph showing a method of measuring a blood pressure using a detected pulse wave signal and reflected pulse wave value ratio.

Referring to FIGS. 14 and 20, in step S7, the main processor 710 may detect blood pressure information including the DBP and the SBP by analyzing the pulse wave value ratio (RI ratio) and the pulse wave value ratio data RIL(RI) in the period during which the peak detection value PK of the pulse wave signal is not detected.

According to one exemplary embodiment, in the period during which the peak detection value PK of the pulse wave signal is not detected, the main processor 710 may set, as the DBP when the heart relaxes, a blood pressure value according to the pulse wave signal detection value at the start time Rip (or PT) of the rapid change period B2 during which the pulse wave value ratio (RI ratio) rapidly changes. Further, the main processor 710 may set, as the SBP when the heart contracts, a blood pressure value according to the pulse wave signal detection value at the start time Ris of the second period B3, during which the pulse wave value ratio (RI ratio) changes with little variation. Further, the main processor 710 may set as the MBP any one pulse wave signal detection value in a period during which the pulse wave value ratio (RI ratio) is in the saturated state to change with little variation.

Figure 21:
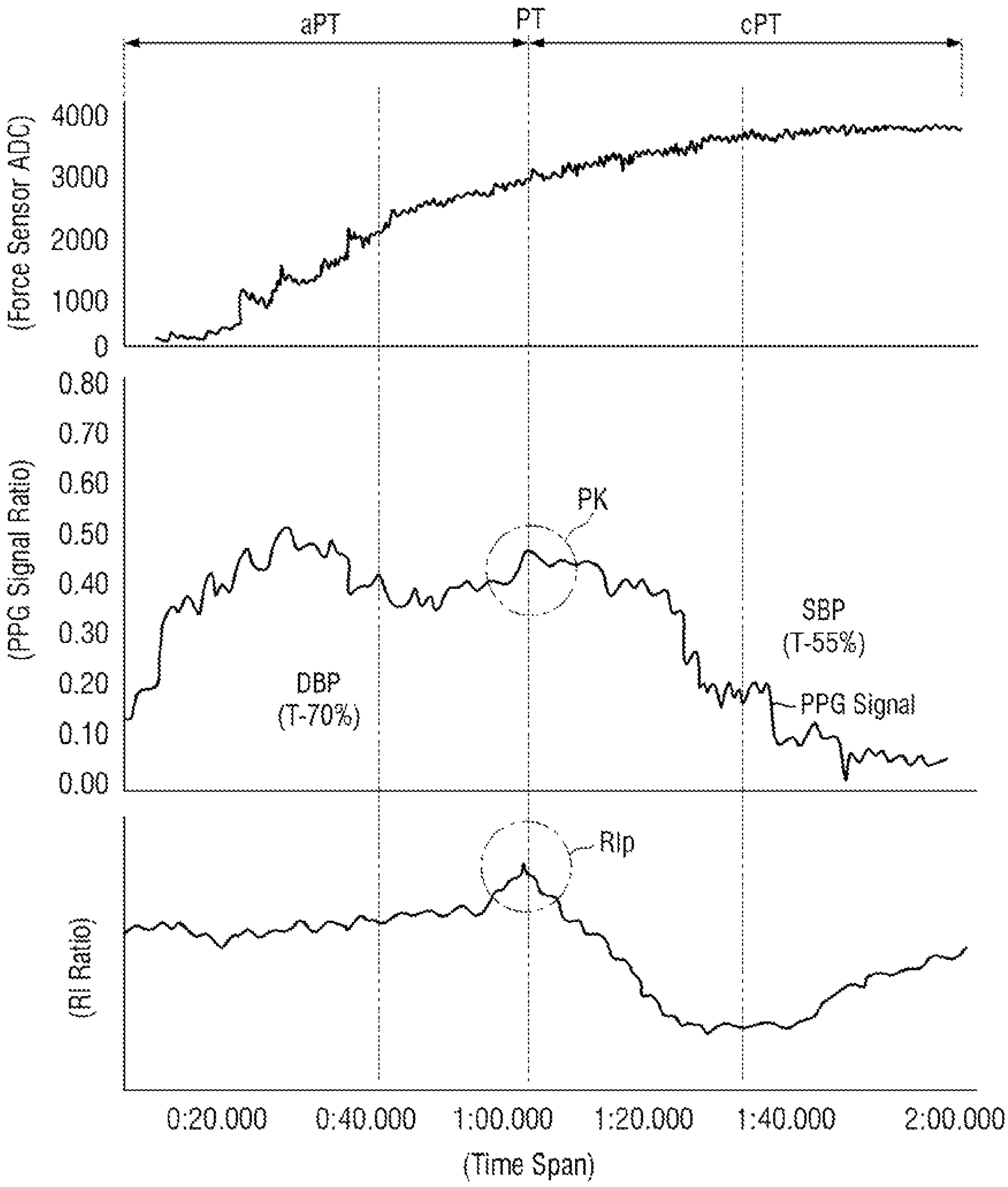
FIG. 21 is a graph showing a method of measuring a blood pressure using a pulse wave signal and a reflected pulse wave value ratio according to another embodiment.

FIG. 21 is a graph showing a method of measuring a blood pressure using a pulse wave signal and a reflected pulse wave value ratio according to another embodiment.

Referring to FIG. 21 in conjunction with FIG. 14, the main processor 710 may set as the DBP the blood pressure value according to the pulse wave signal detection value at about 70 percent of a predetermined previous period aPT before the start time Rip (or PT) at which the pulse wave value ratio rapidly changes. Further, the main processor 710 may set as the SBP the blood pressure value according to the pulse wave signal detection value at about 50 percent of a subsequent period cPT after the second period B3 during which the pulse wave value ratio (RI ratio) changes with little variation.

Further, the main processor 710 may set as the DBP the blood pressure value according to the pulse wave signal detection value, which is about 70 percent of the peak detection value PK, in the predetermined previous period aPT before the time Rip (or PT) at which the pulse wave value ratio (RI ratio) decreases. Further, in step S8, the main processor 710 may set as the SBP the blood pressure value according to the pulse wave signal detection value, which is about 50 percent of the peak detection value PK, in the predetermined subsequent period cPT after the time Rip (or PT) at which the pulse wave value ratio (RI ratio) decreases. Further, the MBP according to the minimum to maximum pressure values may be set.

Among the minimum to maximum pressure values set in step S8 of setting the SBP, the DBP, and the MBP, the maximum pressure value may be set as a systolic blood pressure and the minimum pressure value may be set as a diastolic blood pressure. In this case, information on the SBP, the DBP, and the MBP may be displayed on a preset application program screen on the display panel 300.

Figure 22:
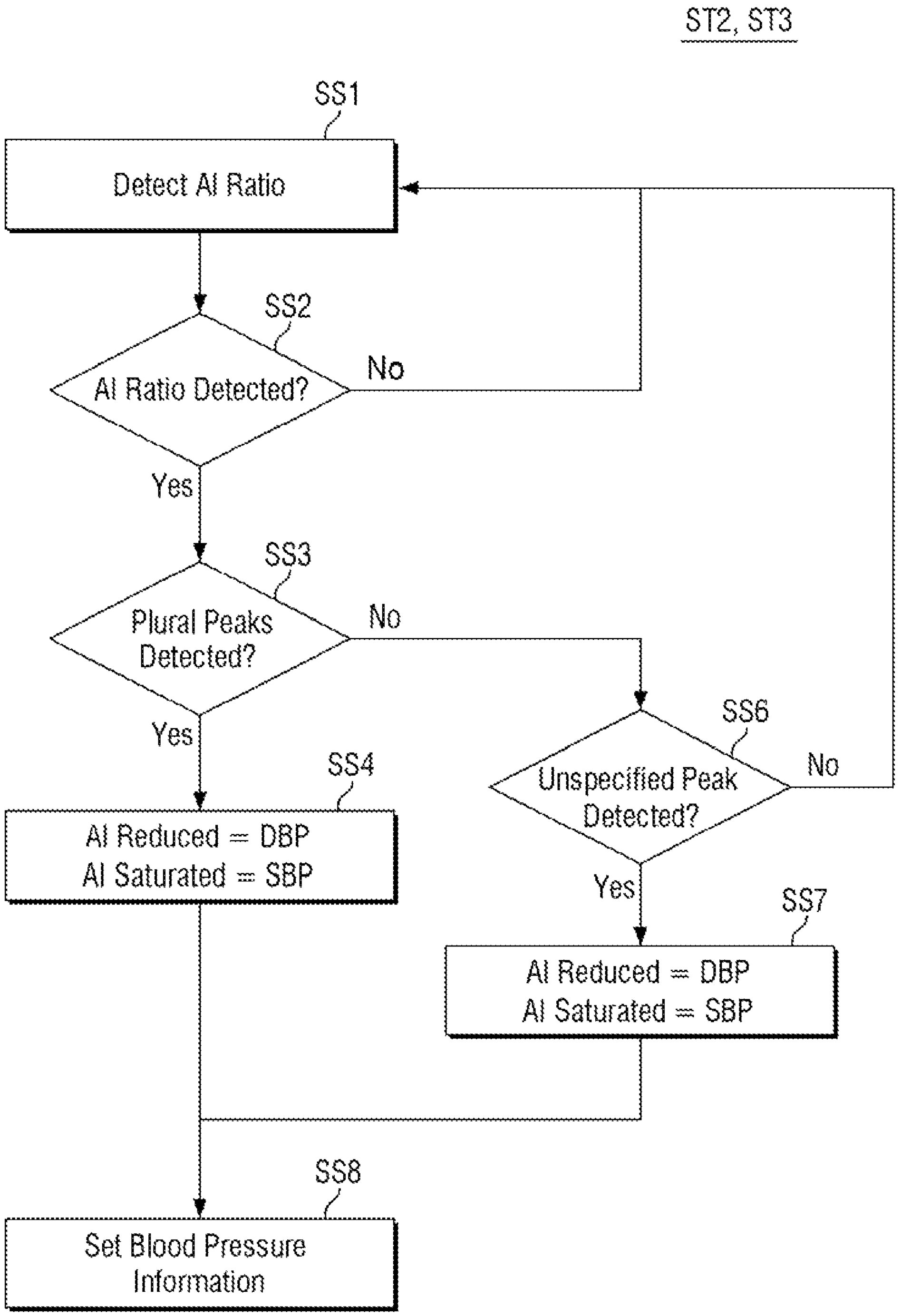
FIG. 22 is a flowchart illustrating a process of detecting a reflected pulse wave difference value and a process of measuring a blood pressure using the reflected pulse wave difference values.
Figure 23:
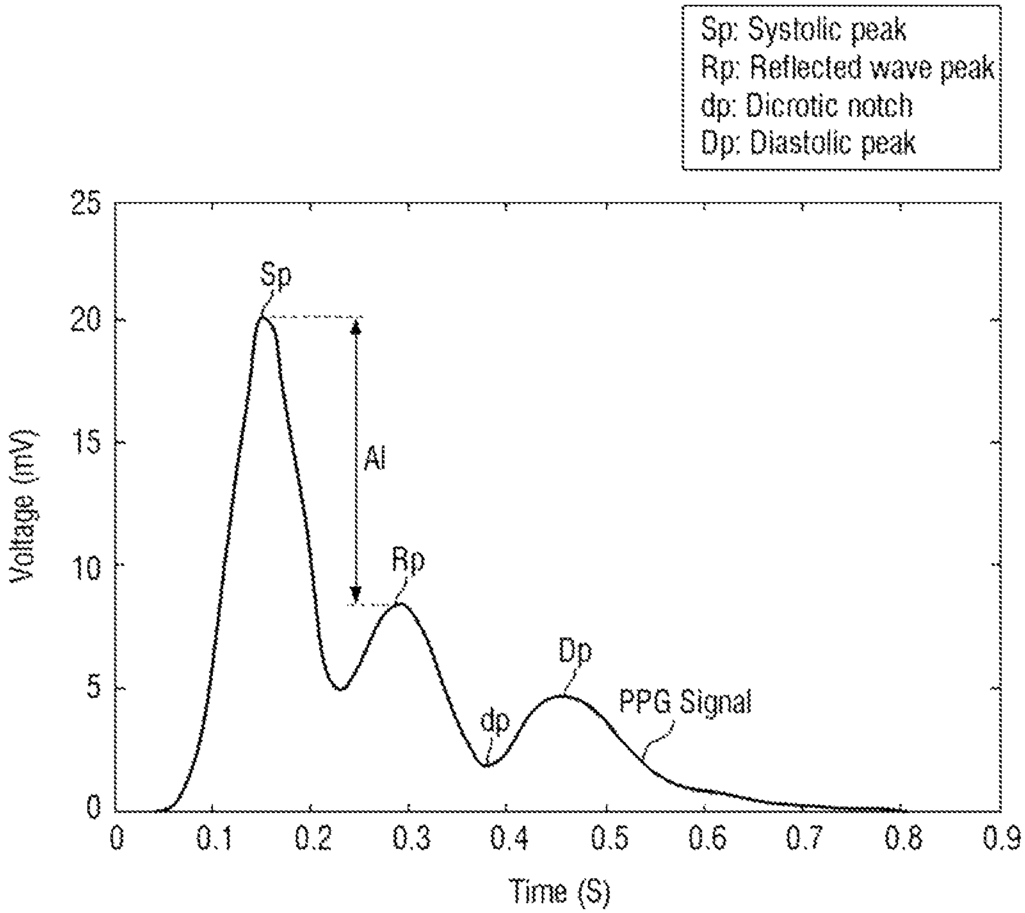
FIG. 23 is a graph illustrating a reflected pulse wave difference value and a method of detecting the reflected pulse wave difference value.

FIG. 22 is a flowchart illustrating a process of detecting a reflected pulse wave difference value and a process of measuring a blood pressure using the reflected pulse wave difference values. FIG. 23 is a graph for explaining a reflected pulse wave difference value and a method of detecting the reflected pulse wave difference value.

Referring to FIGS. 22 and 23, the main processor 710 may detect blood pressure information using reflected pulse wave difference values AI, each of which is a difference value between the highest pulse wave value Sp and the reflected pulse wave value Rp, in an unstable detection period. An unstable detection period of the peak detection value PK at least includes a period during which a plurality of peak detection values PK are detected during the detection period of the peak detection value PK, the peak detection values PK having magnitudes within a range, and a period during which none of the peak detection values PK are detected. The reflected pulse wave difference value AI is a value obtained by detecting the difference between a blood pressure at a time point when the highest pulse wave value Sp is detected and a blood pressure at a time point when the reflected pulse wave value Rp is detected. The reflected pulse wave difference value AI may be used as a factor for measuring disorders of blood perfusion and coronary arteries. Hereinafter, a method of detecting the reflected pulse wave difference values AI for detecting the blood pressure difference will be described in detail with reference to the accompanying drawings.

In order to detect the reflected pulse wave difference values AI, the main processor 710 divides a period of a pulse wave signal generated in real time according to a period in which a wave corresponding to a heartbeat and a reflected wave of a blood vessel sequentially occur. That is, the main processor 710 may set the period of the pulse wave signal as a wave period in which the highest pulse wave value Sp, the reflected pulse wave value Rp, the lowest pulse wave value Dp, and the rebound pulse wave value dp sequentially occur.

In step SS1, the main processor 710 may detect the highest pulse wave value Sp corresponding to a heartbeat and the reflected pulse wave value Rp corresponding to a reflected wave for each divided period of the pulse wave signal, and may detect the reflected pulse wave difference values AI, each of which is the difference between the blood pressure at the time point when the highest pulse wave value Sp is detected and the blood pressure at the time point when the reflected pulse wave value Rp is detected, using Eq. 2 below.

$$AI=(Sp-Rp)/Sp \quad \text{(Eq. 2)}$$

Here, Sp is the highest pulse wave value for each period of the pulse wave signal, and Rp is the reflected pulse wave value detected after the highest pulse wave value.

Then, in step SS2, when the main processor 710 identifies a wave period, wherein the highest pulse wave value Sp, the reflected pulse wave value Rp, the lowest pulse wave value Dp, and the rebound pulse wave value dp sequentially occur in the wave period, the reflected pulse wave difference values AI with respect to the highest pulse wave value are detected for each divided period of the pulse wave signal using Eq. 2.

Figure 24:
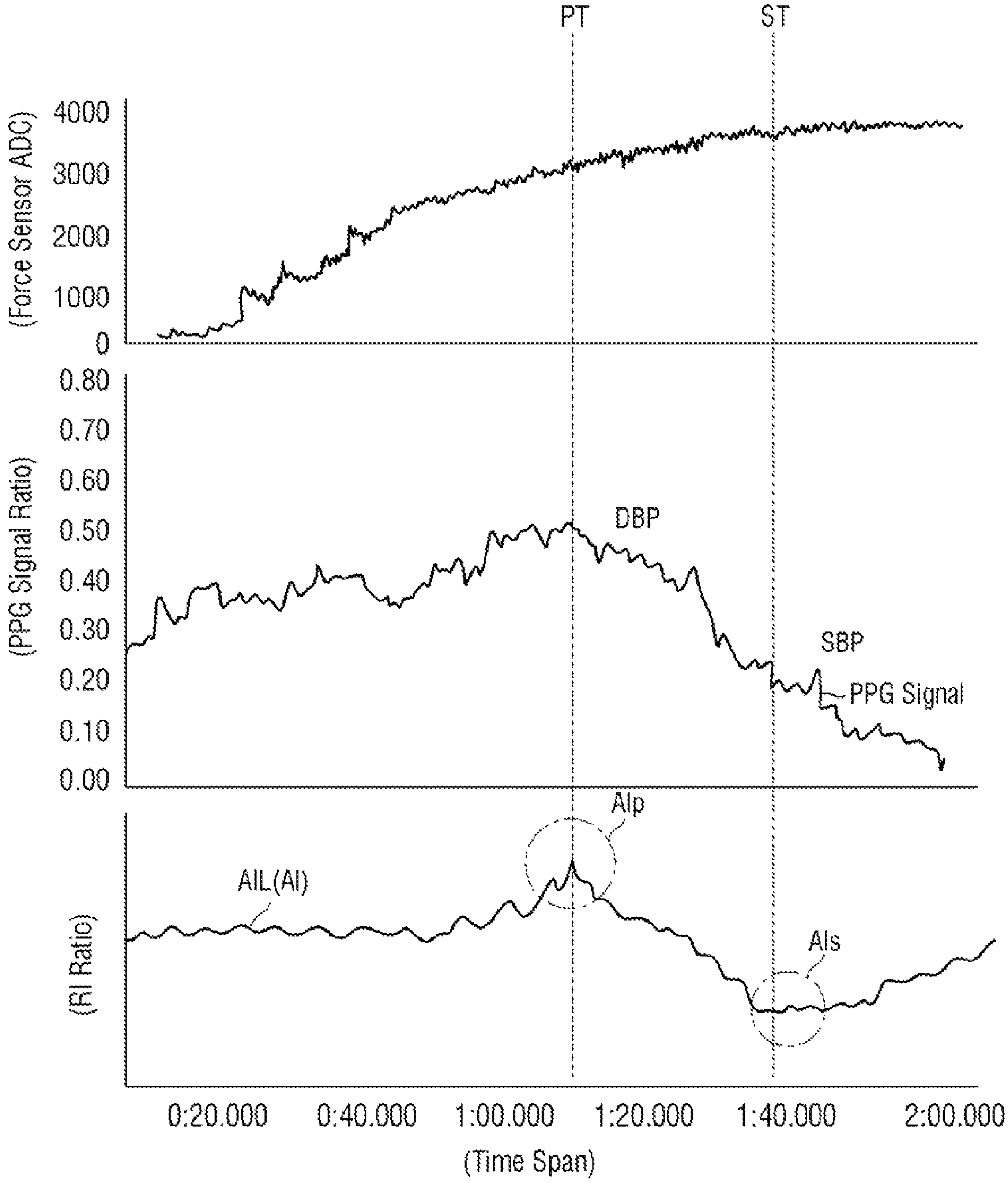
FIG. 24 is a graph illustrating a method of measuring a blood pressure using a detected pulse wave signal and reflected pulse wave difference value.

FIG. 24 is a graph illustrating a method of measuring a blood pressure using a detected pulse wave signal and reflected pulse wave difference value.

Referring to FIG. 24, the main processor 710 sequentially stores detection results of the reflected pulse wave difference values AI with respect to the highest pulse wave value. Then, in step SS3, when it is confirmed that a plurality of peak detection values PK, the peak detection values having magnitudes within a range, have been detected based on the detection result of the peak detection value PK of the pulse wave signal, the sequentially stored reflected pulse wave difference values AI are analyzed. In this case, the main processor 710 may continuously create data of the change in the reflected pulse wave difference values AI with respect to the highest pulse wave value, which has been stored during the detection period of the peak detection value PK, to analyze the change in the size of the reflected pulse wave difference value data AIL(AI).

According to one exemplary embodiment, the main processor 710 may continuously create data of the change in the reflected pulse wave difference values AI with respect to the highest pulse wave value, which has been sequentially generated and stored during the detection period of the peak detection value PK, to analyze the change in the size of the reflected pulse wave difference value data AIL(AI). In this case, the main processor 710 may set as the DBP a blood pressure value according to the pulse wave signal detection value at a start time Aip (or PT), at which the reflected pulse wave difference values AI maintained within a predetermined range rapidly change. Further, the main processor 710 may set as the SBP a blood pressure value according to the pulse wave signal detection value at a start time Ais (or ST) of the second period B3, during which the reflected pulse wave difference value AI changes with little variation. Further, in step SS4, the main processor 710 may set as the MBP any one pulse wave signal detection value in a period during which the reflected pulse wave difference values AI become less variable while converging to a higher or lower saturation state.

In steps SS6 and SS7, In one exemplary embodiment, when the peak detection value PK of the pulse wave signal has not been specified or detected during the detection period of the peak detection value PK. The main processor 710 may continuously create data of the change in the reflected pulse wave difference values AI with respect to the highest pulse wave value, which has been sequentially stored, to analyze the change in the size of the reflected pulse wave difference value data AIL(AI).

In one exemplary embodiment, the main processor 710 may set as the DBP the blood pressure value according to the pulse wave signal detection value at the start time Aip (or PT), at which the reflected pulse wave difference values AI rapidly change. Further, the main processor 710 may set as the SBP the blood pressure value according to the pulse wave signal detection value at the start time Ais (or ST) of the second period, during which the reflected pulse wave difference value AI changes with little variation. Further, in step SS4, the main processor 710 may set as the MBP any one pulse wave signal detection value in a period during which the reflected pulse wave difference values AI are maintained in a higher or lower saturation state.

In one exemplary embodiment, the main processor 710 may set as the DBP a blood pressure value according to the pulse wave signal detection value at about 70 percent of the predetermined previous period aPT before the start time Aip (or PT) at which the reflected pulse wave difference values AI rapidly change. Further, the main processor 710 may set as the SBP a blood pressure value according to the pulse wave signal detection value at about 50 percent of the predetermined subsequent period cPT after the second period during which the reflected pulse wave difference values AI change with little variation.

According to one exemplary embodiment, the main processor 710 may set as the DBP a blood pressure value according to the pulse wave signal detection value, which is about 70 percent of the peak detection value PK, in the predetermined previous period aPT before the time point Aip at which the pulse wave difference value decreases. Further, the main processor 710 may set as the SBP the blood pressure value according to the pulse wave signal detection value, which is about 50 percent of the peak detection value PK, in the predetermined subsequent period cPT after the time point Aip at which the pulse wave difference value decreases. Further, in step SS8, the MBP according to the minimum to maximum pressure values may be set.

Among the minimum to maximum pressure values set in step SS8 of setting the SBP, the DBP, and the MBP, the maximum pressure value may be set as a systolic pressure and the minimum pressure value may be set as a diastolic pressure. In this case, information on the SBP, the DBP, and the MBP may be displayed on the preset application program screen on the display panel 300.

A method of detecting blood pressure information, when the peak detection value PK of the pulse wave signal and time information PT, at which the peak detection value PK is detected, are unclearly calculated, that is, when it is determined that the pulse wave signal is in an unstable state, will be described as follows. An unstable detection period of the peak detection value PK at least includes a period during which a plurality of peak detection values PK are detected during the detection period of the peak detection value PK, the peak detection values PK having magnitudes within a range, and a period during which none of the peak detection values PK are detected.

Referring to FIGS. 12 and 13 referenced above, the main processor 710 detects a pulse wave signal (PPG signal ratio) according to the amount of light sensed by the light receiving sensor 740 and an optical signal corresponding to the amount of light and then detects the peak detection value PK of the pulse wave signal according to the optical signal during a force value calculation period.

When the peak detection value PK of the pulse wave signal and the time information PT, at which the peak detection value PK is detected, are calculated, the main processor 710 determines that the pulse wave signal has been successfully detected. In step ST4, when the peak detection value PK of the pulse wave signal and the time information PT, at which the peak detection value PK is detected, are unclearly calculated, it is determined that the pulse wave signal is in an unstable state.

In step ST5, when the peak detection value PK of the pulse wave signal and the detection time information PT of the peak detection value PK are calculated, each of DBP information, MBP information, and SBP information is calculated by analyzing the pulse wave signal during the previous and subsequent periods aPT and cPT predetermined on the basis of the detection time of the peak detection value PK.

As described above, since the light absorbance has a maximum value when the heart contracts and has a minimum value when the heart relaxes, light sensed by the light receiving sensor 740 may be least when the heart contracts and may be largest when the heart relaxes. Accordingly, the main processor 710 may set, as the DBP when the heart relaxes, a blood pressure value according to the pulse wave signal detection value at any one time in a range of about 60 percent to about 80 percent of the predetermined previous period aPT before the detection time of the peak detection value PK. Further, the main processor 710 may set, as the SBP when the heart contracts, a blood pressure value according to the pulse wave signal detection value at any one time in a range of about 40 percent to about 60 percent of the predetermined subsequent period cPT after the detection time of the peak detection value PK.

For example, the main processor 710 may set, as the DBP when the heart relaxes, the blood pressure value according to the pulse wave signal detection value at about 70 percent of the predetermined previous period aPT before the detection time of the peak detection value PK. Further, the main processor 710 may set, as the SBP when the heart contracts, the blood pressure value according to the pulse wave signal detection value at about 50 percent of the predetermined subsequent period cPT after the detection time of the peak detection value PK. Further, the MBP according to the minimum to maximum blood pressure values may be set. In this case, the blood pressure values corresponding to the light amount, the optical signal, or the pulse wave signal detection value are preset in a built-in memory or the like, thereby calculating the blood pressure values corresponding to the pulse wave signal detection value. In step ST8, the main processor 710 may display information on the SBP, the DBP, and the MBP, which have been calculated and set, on the preset application program screen on the display panel 300.

Step ST3 of setting the SBP, the DBP, and the MBP may be set by various other methods disclosed in Korean Patent Application Publication Nos. 10-2018-0076050, 10-2017-0049280, 10-2019-0040527, and the like in addition to the method illustrated in FIG. 13. The disclosures of the patent applications may be incorporated herein by reference in their entirety.

Figure 25:
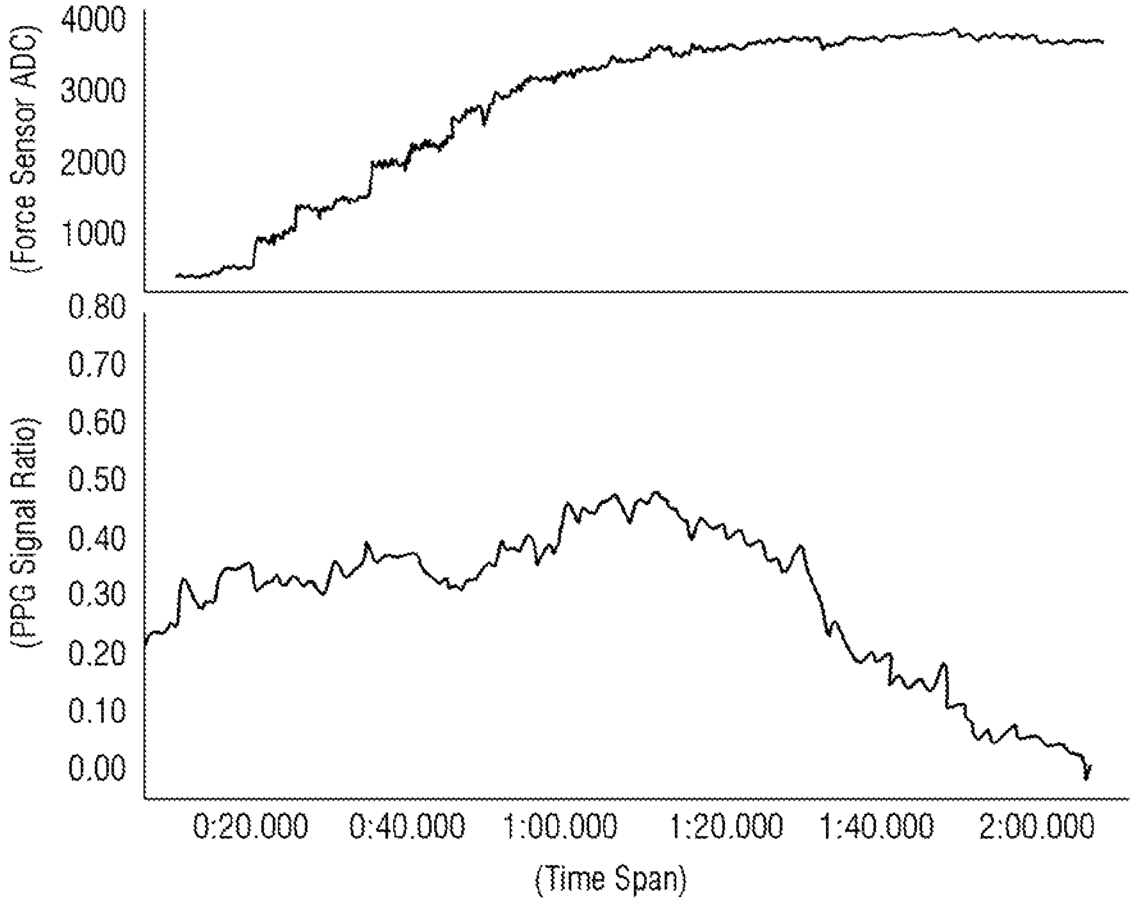
FIG. 25 is a graph illustrating an inaccurately detected pulse wave signal whose peak value has not been specified.

FIG. 25 is a graph illustrating an inaccurately detected pulse wave signal whose peak value has not been specified.

Referring to FIG. 25, in ST2, the main processor 710 detects the peak detection value PK of the pulse wave signal and the time information PT at which the peak detection value PK is detected. In some cases, the main processor 710 may not detect the peak detection value PK of the pulse wave signal in step ST2; in some other cases, the main processor 710 may not determine a definite value for the peak detection value PK. In other words, when a plurality of detection values of the pulse wave signal are detected to have similar specific peak magnitudes, any one peak detection value PK may not be set, and the time information PT, at which the peak detection value PK is detected, may also not be detected.

In step ST4, when the peak detection value PK of the pulse wave signal is not detected and set, the main processor 710 calculates the lowest pulse wave signal value during the detection period of the peak detection value PK of the pulse wave signal. For example, if the peak detection value PK of the pulse wave signal is not set, the main processor 710 may detect the lowest pulse wave signal during a preset previous period and a preset subsequent period on the basis of a time point when the plurality of detection values of the pulse wave signal are detected to have similar specific peak magnitudes. Particularly, the main processor 710 may calculate an average pulse wave signal value during the detection period of the peak detection value PK in addition to detecting the lowest pulse wave signal value among the pulse wave signal detection values detected during the detection period of the peak detection value PK.

In step ST5, when the average pulse wave signal value and the lowest pulse wave signal value are detected, the main processor 710 may set the MBP corresponding to the average pulse wave signal value and set the DBP corresponding to the lowest pulse wave signal value. Then, it may set the SBP and reset the DBP using Eq. 3 below.

$$SBP=\alpha\times MBP-\beta\times DBP$$

$$DBP=(\alpha\times MBP-SBP)/\beta \quad \text{(Eq. 3)}$$

Here, α and β are natural numbers except zero, which are equal to or different from each other. Accordingly, in step ST8, the information on the SBP, the DBP, and the MBP set using Eq. 3 may be displayed on the preset application program screen on the display panel 300.

Figure 26:
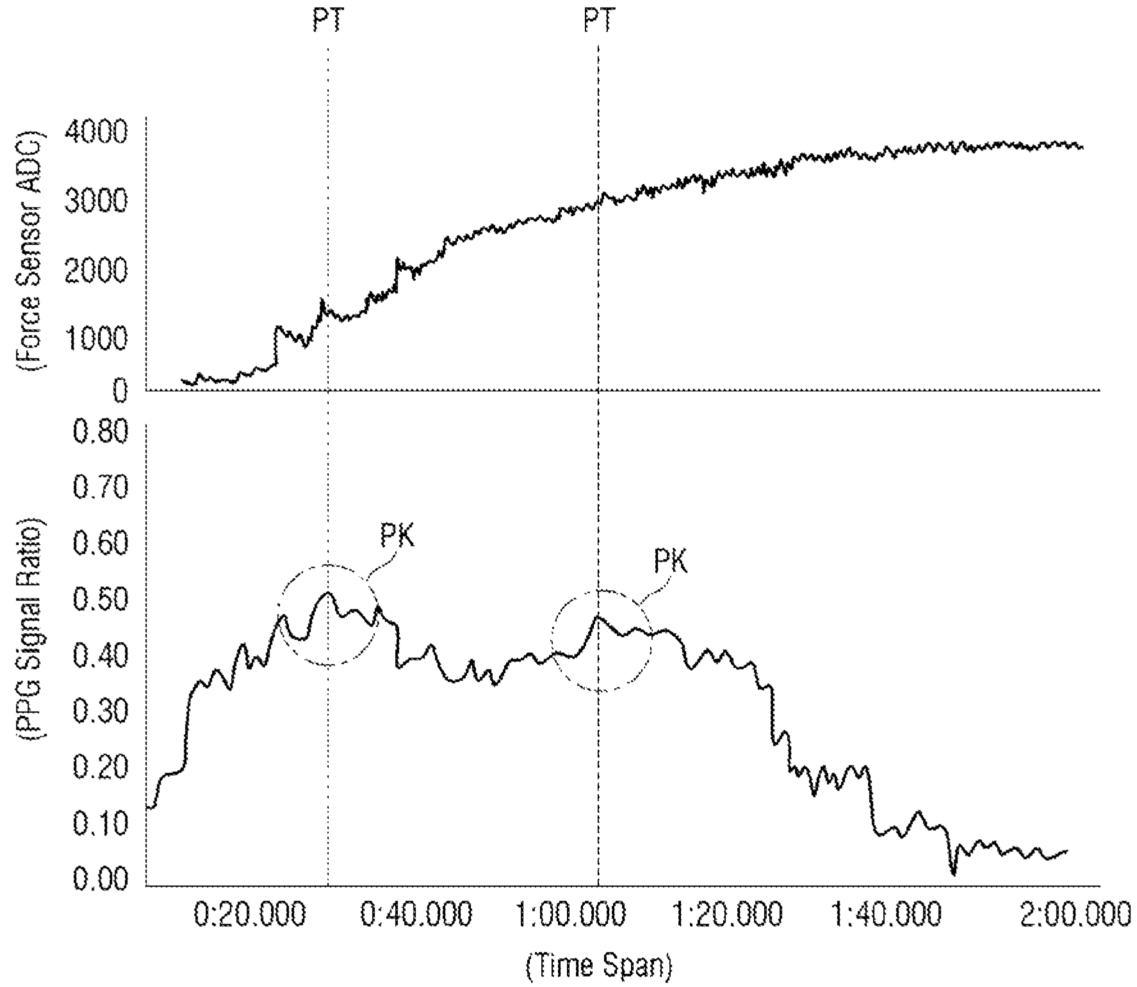
FIG. 26 is a graph showing an inaccurately detected pulse wave signal in which a plurality of peak values have been specified.

FIG. 26 is a graph showing an inaccurately detected pulse wave signal in which a plurality of peak values have been specified.

Referring to FIG. 26, as a plurality of peak detection values PK are detected during the detection period of the peak detection value PK, the main processor 710 may not set the time information PT at which the peak detection value PK is detected. For example, when a plurality of peak detection values PK are detected during the detection period of the peak detection value PK, the peak detection value PK of the pulse wave signal may not be set, and the time information PT, at which the peak detection value PK is detected, may also not be set.

In one exemplary embodiment, the main processor 710 may detect the lowest pulse wave signal value in the detection period of the peak detection value PK even when the peak detection value PK of the pulse wave signal is not set or the time information PT, at which the detection value PK is detected, is not specified. In addition, the average pulse wave signal value during the detection period of the peak detection value PK may be detected.

When the average pulse wave signal value and the lowest pulse wave signal value are detected, the main processor 710 may set the MBP corresponding to the average pulse wave signal value and set the DBP corresponding to the lowest pulse wave signal value. In step ST5, it may reset the SBP and reset the DBP using Eq. 3 above.

Figure 27:
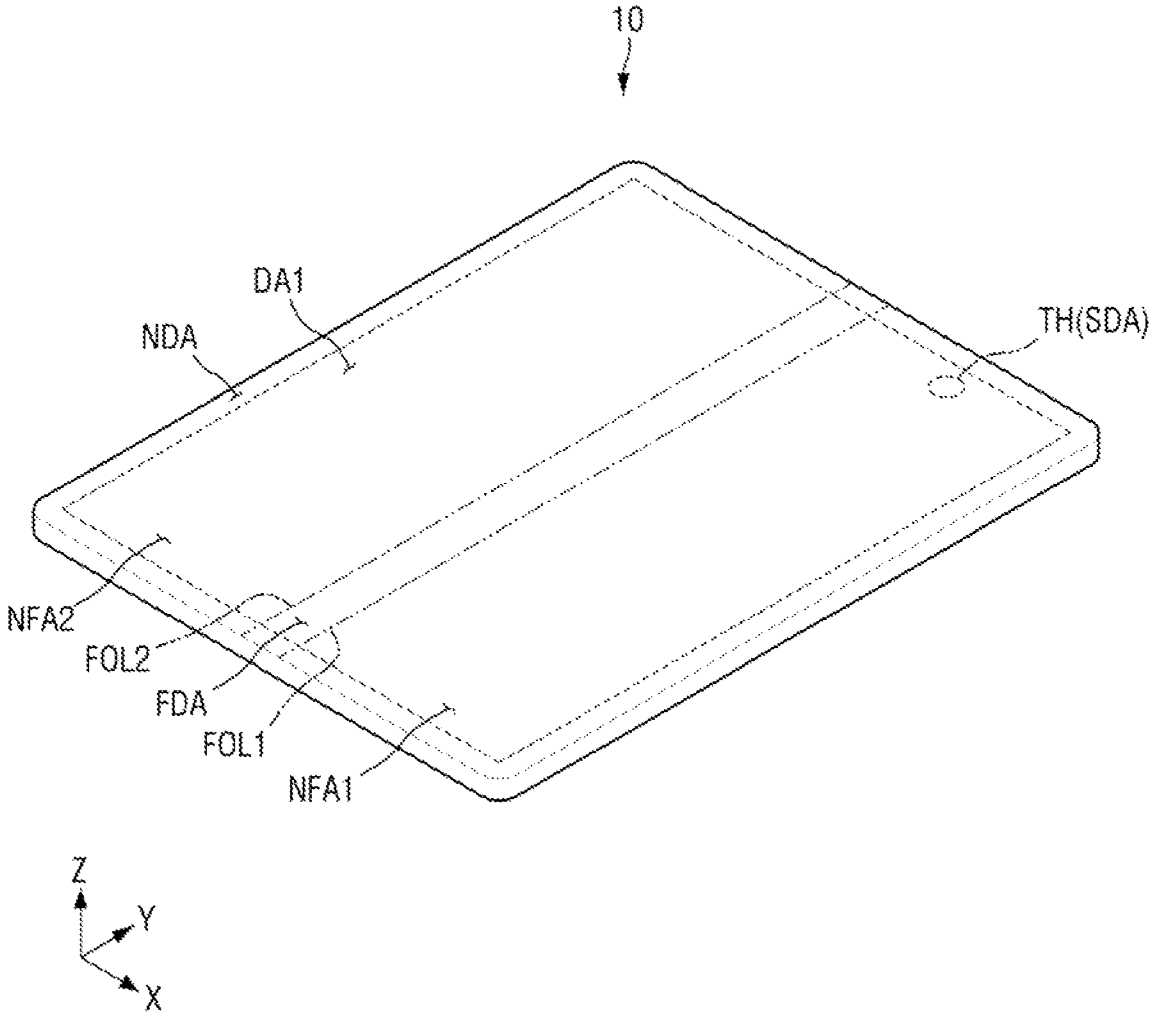
FIGS. 27 and 28 are perspective views illustrating a display device according to another embodiment of the present disclosure.
Figure 28:
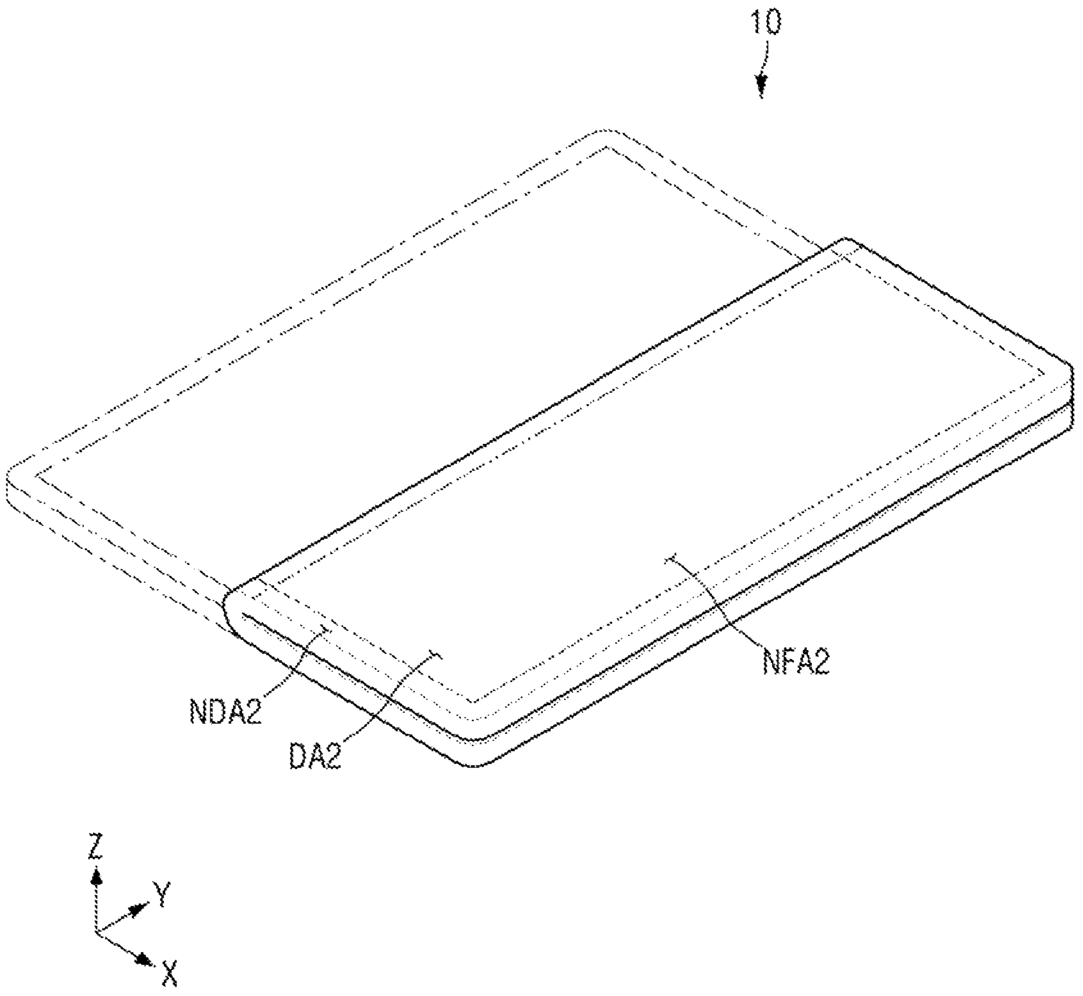

FIGS. 27 and 28 are perspective views illustrating a display device according to another embodiment of the present disclosure.

FIGS. 27 and 28 illustrate the display device 10 as a foldable display device that is folded in the first direction (X-axis direction). The display device 10 may maintain both a folded state and an unfolded state. The display device 10 may be folded in an in-folding manner in which the front surface is disposed on the inside thereof. When the display device 10 is bent or folded in the in-folding manner, the front surfaces of the display device 10 may be disposed to face each other. Alternatively, the display device 10 may be folded in an out-folding manner in which the front surface is disposed on the outside thereof. When the display device 10 is bent or folded in the out-folding manner, the rear surfaces of the display device 10 may be disposed to face each other.

A first non-folding area NFA1 may be disposed on one side, for example, the right side of a folding area FDA. In the same example, a second non-folding area NFA2 may be disposed on the other side, for example, the left side of the folding area FDA.

in one exemplary embodiment, a first folding line FOL1 and a second folding line FOL2 may be configured to extend in the second direction (Y-axis direction), and the display device 10 may be folded in the first direction (X-axis direction). Accordingly, the length of the display device 10 in the first direction (X-axis direction) may be reduced to approximately half.

In one exemplary embodiment, the extension direction of the first folding line FOL1 and the extension direction of the second folding line FOL2 are not necessarily limited to the second direction (Y-axis direction). For example, the first folding line FOL1 and the second folding line FOL2 may extend in the first direction (X-axis direction), and the display device 10 may be folded in the second direction (Y-axis direction). In this case, the length of the display device 10 in the second direction (Y-axis direction) may be reduced to approximately half. Alternatively, the first folding line FOL1 and the second folding line FOL2 may extend in the diagonal direction of the display device 10 between the first direction (X-axis direction) and the second direction (Y-axis direction). In this case, the display device 10 may be folded in a triangular shape.

According to one exemplary embodiment, when the first folding line FOL1 and the second folding line FOL2 extend in the second direction (Y-axis direction), the length of the folding area FDA in the first direction (X-axis direction) may be shorter than the length thereof in the second direction (Y-axis direction). Further, the length of the first non-folding area NFA1 in the first direction (X-axis direction) may be longer than the length of the folding area FDA in the first direction (X-axis direction). The length of the second non-folding area NFA2 in the first direction (X-axis direction) may be longer than the length of the folding area FDA in the first direction (X-axis direction).

in one exemplary embodiment, a first display area DA1 may be disposed on the front surface of the display device 10. The first display area DA1 may overlap the folding area FDA, the first non-folding area NFA1, and the second non-folding area NFA2. In this case, when the display device 10 is unfolded, an image may be displayed toward the front side thereof in the folding area FDA, the first non-folding area NFA1, and the second non-folding area NFA2 of the display device 10.

A second display area DA2 may be disposed on the rear surface of the display device 10. The second display area DA2 may overlap the second non-folding area NFA2. In this case, when the display device 10 is folded, an image may be displayed toward the front side thereof in the second non-folding area NFA2 of the display device 10.

FIGS. 27 and 28 illustrate that the through hole TH or the sub-display area SDA is disposed in the first non-folding area NFA1, but the present disclosure is not necessarily limited thereto. For example, the through hole TH or the sub-display area SDA may be disposed in the second non-folding area NFA2 or the folding area FDA.

Figure 29:
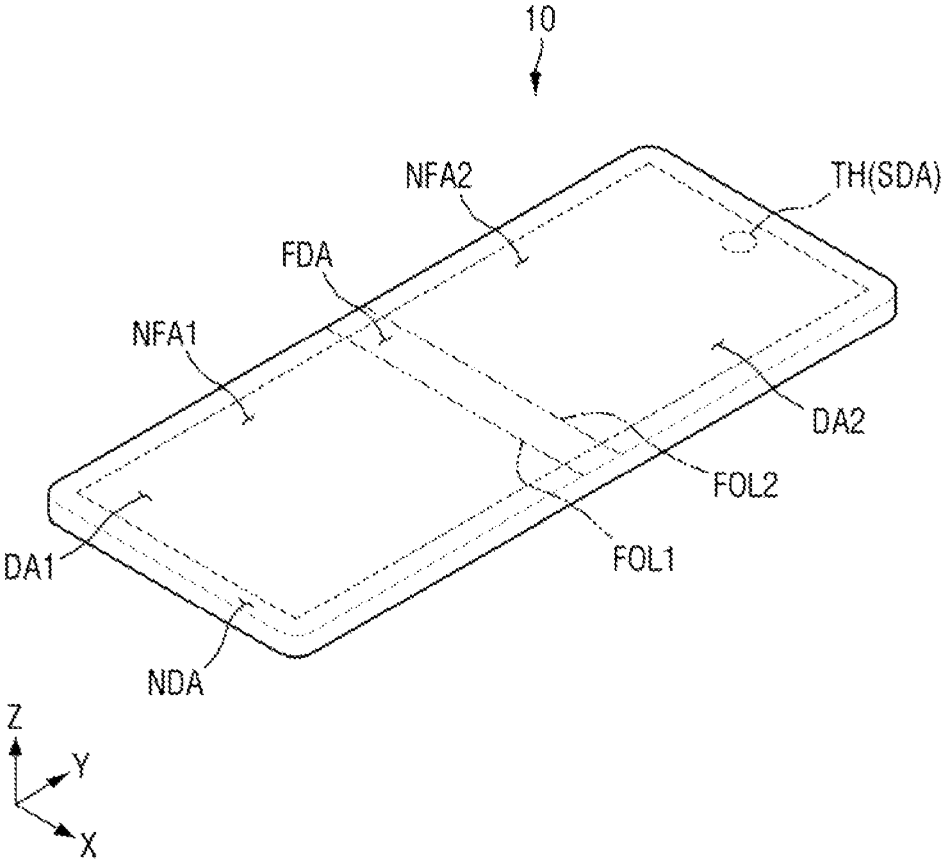
FIGS. 29 and 30 are perspective views illustrating a display device according to another embodiment of the present disclosure.
Figure 30:
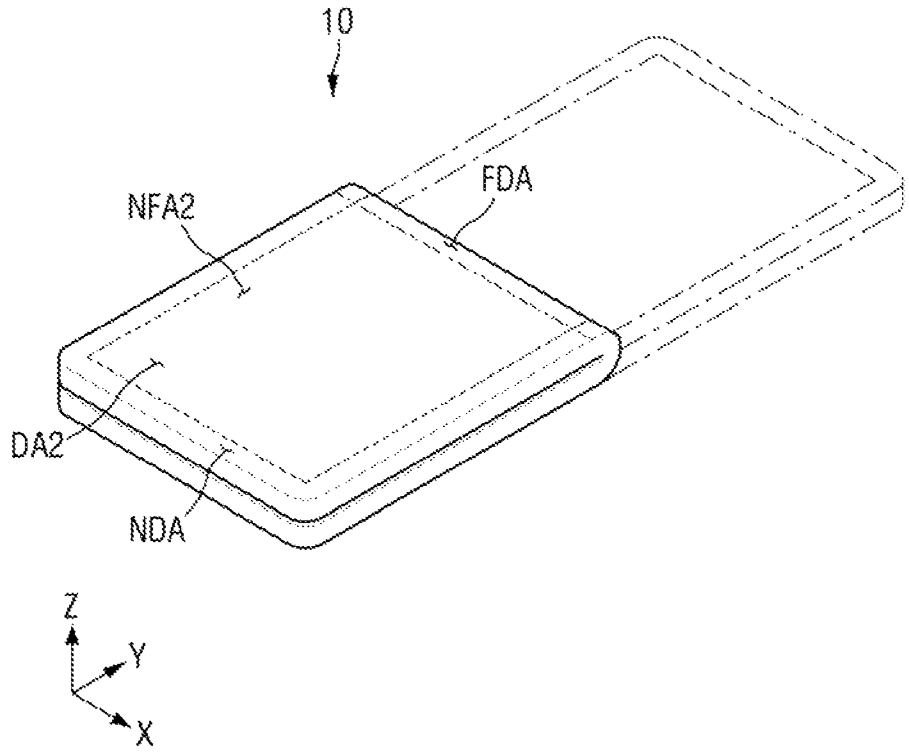

FIGS. 29 and 30 are perspective views illustrating a display device according to another embodiment of the present disclosure.

FIGS. 29 and 30 illustrate the display device 10 as a foldable display device that is folded in the second direction (Y-axis direction). The display device 10 may maintain both a folded state and an unfolded state. The display device 10 may be folded in an in-folding manner in which the front surface is disposed on the inside thereof. For example, when the display device 10 is bent or folded in an in-folding manner, the front surfaces of the display device 10 may be disposed to face each other. In another example, the display device 10 may be folded in an out-folding manner in which the front surface is disposed on the outside. When the display device 10 is bent or folded in an out-folding manner, the rear surfaces of the display device 10 may be disposed to face each other.

The display device 10 may include, for example, a folding area FDA, the first non-folding area NFA1, and the second non-folding area NFA2. The folding area FDA may be an area in which the display device 10 is folded, and the first and second non-folding areas NFA1 and NFA2 may be areas in which the display device 10 is not folded.

The first non-folding area NFA1 may be disposed on one side (e.g., a lower side) of the folding area FDA. The second non-folding area NFA2 may be disposed on the other side (e.g., an upper side) of the folding area FDA. The folding area FDA may be a curved area with a predetermined curvature at a first folding line FOL1 and a second folding line FOL2. Thus, the first folding line FOL1 may be the boundary between the folding area FDA and the first non-folding area NFA1, and the second folding line FOL2 may be the boundary between the folding area FDA and the second non-folding area NFA2.

The first folding line FOL1 and the second folding line FOL2 may extend in the first direction (X-axis direction) as shown in FIGS. 27 and 28. In this case, the display device 10 may be folded in the second direction (Y-axis direction). Accordingly, the length of the display device 10 in the second direction (Y-axis direction) may be reduced to approximately half, so that a user can conveniently carry the display device 10.

In one exemplary embodiment, the extension direction of the first folding line FOL1 and the extension direction of the second folding line FOL2 is not necessarily limited to the first direction (X-axis direction). For example, the first folding line FOL1 and the second folding line FOL2 may extend in the second direction (Y-axis direction), and the display device 10 may be folded in the first direction (X-axis direction). In this case, the length of the display device 10 in the first direction (X-axis direction) may be reduced to approximately half. In another example, the first folding line FOL1 and the second folding line FOL2 may extend in the diagonal direction of the display device 10 between the first direction (X-axis direction) and the second direction (Y-axis direction). In this case, the display device 10 may be folded in a triangular shape.

When the first folding line FOL1 and the second folding line FOL2 extend in the first direction (X-axis direction) as shown in FIGS. 29 and 30, the length of the folding area FDA in the second direction (Y-axis direction) may be shorter than the length of the folding area FDA in the first direction (X-axis direction). Further, the length of the first non-folding area NFA1 in the second direction (Y-axis direction) may be longer than the length of the folding area FDA in the second direction (Y-axis direction). The length of the second non-folding area NFA2 in the second direction (Y-axis direction) may be longer than the length of the folding area FDA in the second direction (Y-axis direction).

The first display area DA1 may be disposed on the front surface of the display device 10. The first display area DA1 may overlap the folding area FDA, the first non-folding area NFA1, and the second non-folding area NFA2. Therefore, when the display device 10 is unfolded, an image may be displayed toward the front side thereof in the folding area FDA, the first non-folding area NFA1, and the second non-folding area NFA2 of the display device 10.

The second display area DA2 may be disposed on the rear surface of the display device 10. The second display area DA2 may overlap the second non-folding area NFA2. Therefore, when the display device 10 is folded, an image may be displayed toward the front side thereof in the second non-folding area NFA2 of the display device 10.

FIGS. 29 and 30 illustrate that the through hole TH or the sub-display area SDA is disposed in the first non-folding area NFA1, but the present disclosure is not necessarily limited thereto. The through hole TH or the sub-display area SDA may be disposed in the second non-folding area NFA2 or the folding area FDA.

In concluding the detailed description, those skilled in the art will appreciate that many variations and modifications can be made to the preferred embodiments without substantially departing from the principles of the exemplary embodiments of the present inventive concept. Therefore, the disclosed preferred embodiments of the invention are used in a generic and descriptive sense only and not for purposes of limitation.

What is claimed is:

1. A display device comprising:

a display panel comprising a plurality of pixels, the display panel including a through hole penetrating the display panel, the display panel further including a touch electrode layer having touch electrodes for sensing a touch of an object;

a force sensor disposed on a surface of the display panel, distinct from the display panel and the touch electrode layer, the force sensor configured to sense an external force, the force sensor including an optical hole overlapping the through hole in a thickness direction of the display device;

a light receiving sensor configured to sense an amount of light reflected toward the display panel through the through hole of the display panel and the optical hole of the force sensor and generate an optical signal corresponding to the amount of the light;

a main processor configured to generate a pulse wave signal according to the optical signal received from the light receiving sensor and analyze a magnitude, a period, and a wave change of the pulse wave signal; and a light emitting member disposed alongside the light receiving sensor, with both the light emitting member and the light receiving sensor overlapping the optical hole of the force sensor such that the optical hole of the force sensor exposes an entirety of the light emitting member and the light receiving sensor.

2. The display device of claim 1, wherein the main processor is configured to identify a wave period, wherein a highest pulse wave value, a reflected pulse wave value, and a lowest pulse wave value sequentially occur in the wave period, set the period of the pulse wave signal as the wave period, and determine a pulse wave value ratio by using a ratio of the reflected pulse wave value to the highest pulse wave value (RI ratio) during the period of the pulse wave signal.

3. The display device of claim 2, wherein the main processor is configured to generate pulse wave value ratio data by continuously storing and measuring a change in the pulse wave value ratio, and detect, according to the pulse wave value ratio, a first period, a change period, and a second period, wherein during the first period, the pulse wave value ratio fluctuates within a preset range; during the change period, the pulse wave value ratio fluctuates beyond the preset range in a predetermined period; and during the second period, the pulse wave value ratio fluctuates within the preset range, and wherein the second period occurs after the rapid change period.

4. The display device of claim 3, wherein the main processor is configured to detect a start time of the change period and a start time of the second period by analyzing fluctuations of the pulse wave value ratio data, set a blood pressure value according to a pulse wave signal detection value at the start time of the change period as a diastolic blood pressure, set the blood pressure value according to a pulse wave signal detection value at the start time of the second period after the change period as a systolic blood pressure, and set the blood pressure value according to a pulse wave signal detection value in the first period or the second period as a mean blood pressure.

5. The display device of claim 3, wherein the main processor is configured to detect one or more peak detection values of the pulse wave signal and detection time information of the one or more peak detection values, the one or more peak detection values having magnitudes within a range, identify an unstable detection period of peak detection value, wherein during the unstable period of peak detection value, either more than one peak detection values are detected or none of the peak detection values are detected;

detect a start time of the change period and a start time of the second period by analyzing fluctuations of the pulse wave value ratio data during the unstable detection period, set a blood pressure value according to a pulse wave signal detection value at the start time of the change period as a diastolic blood pressure, set the blood pressure value according to a pulse wave signal detection value at the start time of the second period after the change period as a systolic blood pressure, and set the blood pressure value according to a pulse wave signal detection value in the first period or the second period as a mean blood pressure.

6. The display device of claim 3, wherein the main processor is configured to determine a previous period before the start time of the change period and a subsequent period after the start time of the second period, set, as a diastolic blood pressure, a blood pressure value according to a pulse wave signal detection value at 70 percent of the previous period before the start time of the change period, set, as a systolic blood pressure, the blood pressure value according to a pulse wave signal detection value at a given percent of the subsequent period after the start time of the second period, and set a mean blood pressure according to the diastolic blood pressure and the systolic blood pressure.

7. The display device of claim 3, wherein the main processor is configured to detect a peak detection value of the pulse wave, determine a previous period before the start time of the change period and a subsequent period after the start time of the second period, set, as a diastolic blood pressure, a blood pressure value according to a pulse wave signal detection value, in the previous period before the start time of the change period, wherein the pulse wave signal detection value is 70 percent of the peak detection value, set, as a systolic blood pressure, the blood pressure value according to a pulse wave signal detection value, in the subsequent period after the start time of the second period, wherein the pulse wave signal detection value is a given percent of the peak detection value, and set a mean blood pressure according to the diastolic blood pressure and the systolic blood pressure.

8. The display device of claim 1, wherein the main processor is configured to identify a wave period, wherein a highest pulse wave value, a reflected pulse wave value, and a lowest pulse wave value sequentially occur in the wave period, set the period of the pulse wave signal as the wave period, and determine reflected pulse wave difference values, wherein each of the reflected pulse wave difference values is a difference between a blood pressure at a time point when the highest pulse wave value is detected and a blood pressure at a time point when the reflected pulse wave value is detected during the wave period of the pulse wave signal.

9. The display device of claim 8, wherein the main processor is configured to generate reflected pulse wave difference value data by continuously storing and measuring a change in the reflected pulse wave difference values, and detect, according to the reflected pulse wave difference value data, a first period, a change period, and a second period, wherein during the first period, the reflected pulse wave difference value fluctuates within a preset range, during the change period, the reflected pulse wave difference value fluctuates beyond the preset range in a predetermined period, and during the second period, the reflected pulse wave difference value fluctuates within the preset range, and wherein the second period occurs after the change period.

10. The display device of claim 9, wherein the main processor is configured to detect a start time of the change period and a start time of the second period by analyzing fluctuations of the reflected pulse wave difference value data, set a blood pressure value according to a pulse wave signal detection value at the start time of the change period as a diastolic blood pressure, set the blood pressure value according to a pulse wave signal detection value at the start time of the second period after the change period as a systolic blood pressure, and set the blood pressure value according to a pulse wave signal detection value in the first period or the second period as a mean blood pressure.

11. The display device of claim 9, wherein the main processor is configured to detect one or more peak detection values of the pulse wave signal and detection time information of the one or more peak detection values, detect a start time of the change period by analyzing a change in size of the reflected pulse wave difference value data, wherein a plurality of the peak detection values of the pulse wave signal are detected, or none is detected during the change period, set a blood pressure value according to a pulse wave signal detection value at the start time of the change period as a diastolic blood pressure, set the blood pressure value according to a pulse wave signal detection value at the start time of the second period after the change period as a systolic blood pressure, and sets the blood pressure value according to a pulse wave signal detection value in the first period or the second period as a mean blood pressure.

12. The display device of claim 9, wherein the main processor is configured to set, as a diastolic blood pressure, a blood pressure value according to a pulse wave signal detection value at 70 percent of a predetermined previous period before a start time of the change period, set, as a systolic blood pressure, the blood pressure value according to a pulse wave signal detection value at a given percent of a predetermined subsequent period after a start time of the second period, and set a mean blood pressure according to the diastolic blood pressure and the systolic blood pressure.

13. The display device of claim 1, wherein the main processor is configured to calculate a peak detection value of the pulse wave signal and detection time information of the peak detection value, and calculate diastolic blood pressure information, mean blood pressure information, and systolic blood pressure information by analyzing pulse wave signal values during previous and subsequent periods predetermined based on a detection time of the peak detection value.

14. The display device of claim 13, wherein the main processor is configured to set, as a diastolic blood pressure, a blood pressure value according to a pulse wave signal detection value at a time in a range of 60 percent to 80 percent of a predetermined previous period before the detection time of the peak detection value, set, as a systolic blood pressure, the blood pressure value according to a pulse wave signal detection value at a time in a range of 40 percent to 60 percent of a predetermined subsequent period after the detection time of the peak detection value, and set a mean blood pressure according to the diastolic blood pressure and the systolic blood pressure.

15. The display device of claim 13, wherein the main processor is configured to set, as a diastolic blood pressure, a blood pressure value according to a pulse wave signal detection value, wherein the pulse wave signal detection value is 70 percent of the peak detection value, in a predetermined previous period before the detection time of the peak detection value, set, as a systolic blood pressure, the blood pressure value according to a pulse wave signal detection value, wherein the pulse wave signal detection value is a given percent of the peak detection value, in a predetermined subsequent period after the detection time of the peak detection value, and set a mean blood pressure according to the diastolic blood pressure and the systolic blood pressure.

16. The display device of claim 13, wherein the main processor is configured to calculate a lowest pulse wave signal value and an average pulse wave signal value during a detection period of the peak detection value, wherein the peak detection value of the pulse wave signal is not detected or set, set, as a mean blood pressure, a blood pressure value corresponding to the average pulse wave signal value, and set or reset the systolic blood pressure (SBP) and the diastolic blood pressure (DBP), wherein SBP equals a difference between a times of the mean blood pressure (MBP) and β times of DBP, wherein a and β are natural numbers.

17. The display device of claim 1, wherein the light emitting member and the light receiving sensor overlap the through hole of the display panel and the optical hole of the force sensor in the thickness direction of the display panel such that the through hole of the display panel and the optical hole of the force sensor expose an entirety of the light emitting member and the light receiving sensor, and wherein the light receiving sensor is configured to sense light reflected by a body part or an object on another surface opposite to the surface of the display panel, and wherein the light reflected by the body part or the object includes at least part of light emitted from the light emitting member through the through hole and the optical hole.

18. The display device of claim 17, wherein the force sensor comprises:

a first base substrate and a second base substrate, the first base substrate and the second base substrate facing each other;

a first force sensor electrode disposed on the first base substrate;

a second force sensor electrode disposed on the second base substrate; and a force sensing layer overlapping the first force sensor electrode and the second force sensor electrode in a thickness direction of the first base substrate.

19. The display device of claim 1, further comprising:

a main circuit board disposed below the force sensor, the force sensor being disposed between the display panel and the main circuit board; and a bracket disposed between the main circuit board and the force sensor, wherein the bracket includes a sensor hole overlapping the through hole of the display panel and the optical hole of the force sensor in the thickness direction of the display device, and wherein the light receiving sensor is disposed within the sensor hole of the bracket.

20. The display device of claim 19, wherein the light emitting member and the light receiving sensor overlap the through hole of the display panel and the optical hole of the force sensor in the thickness direction of the display device such that the through hole of the display panel and the optical hole of the force sensor expose an entirety of the light emitting member and the light receiving sensor, and wherein the light emitting member is disposed within the sensor hole of the bracket.

21. A method for using a display device including:

receiving a force signal from a force sensor disposed under a display panel that includes a touch electrode layer having touch electrodes for sensing a touch of an object, the force sensor being distinct from the display panel and the touch electrode layer, the force sensor generating the force signal based on an external force;

emitting light from a light emitting member disposed under the display panel and the force sensor;

receiving an optical signal from a light receiving sensor disposed under the display panel and the force sensor, the optical signal sensing an amount of light emitted from the light emitting member and reflected off an object disposed above the display panel through a through hole penetrating the display panel and an optical hole penetrating through the force sensor and generating the optical signal corresponding to the amount of the light, wherein the optical hole of the force sensor exposes an entirety of the light emitting member and the light receiving sensor;

generating, using a main processor, a pulse wave signal according to the optical signal;

determining, using the main processor, a period of the pulse wave signal by identifying a wave period, wherein a highest pulse wave value, a reflected pulse wave value, and a lowest pulse wave value sequentially occur in the wave period;

determining, using the main processor, a plurality of benchmarks including at least a pulse wave value ratio and a reflected pulse wave difference, wherein the pulse wave value ratio is determined based on a ratio of the reflected pulse wave value to the highest pulse wave value (RI ratio) during the period of the pulse wave signal, and the reflected pulse wave difference is determined based on a difference between a blood pressure at a time point when the highest pulse wave value is detected and a blood pressure at a time point when the reflected pulse wave value is detected;

generating, using the main processor, benchmark data by continuously storing and measuring a change in a benchmark;

detecting, using the main processor, a start time of a change period and a start time of a second period by analyzing fluctuations of the benchmark;

setting, using the main processor, a diastolic blood pressure according to a pulse wave signal detection value at the start time of the change period;

setting, using the main processor, a systolic blood pressure according to a pulse wave signal detection value at a start time of the second period after the change period; and setting, using the main processor, a mean blood pressure according to a pulse wave signal detection value in either the period of the pulse wave signal or the second period.

22. An electronic device, comprising:

a display device including:

a display panel comprising a plurality of pixels, the display panel including a through hole penetrating the display panel, the display panel further including a touch electrode layer having touch electrodes for sensing a touch of an object;

a force sensor disposed on a surface of the display panel, distinct from the display panel and the touch electrode layer, the force sensor configured to sense an external force, the force sensor including an optical hole overlapping the through hole in a thickness direction of the display device;

a light receiving sensor configured to sense an amount of light reflected toward the display panel through the through hole of the display panel and the optical hole of the force sensor and generate an optical signal corresponding to the amount of the light; and a light emitting member disposed alongside the light receiving sensor, with both the light emitting member and the light receiving sensor overlapping the optical hole of the force sensor such that the optical hole of the force sensor exposes an entirety of the light emitting member and the light receiving sensor, wherein the electronic device further includes a main processor configured to generate a pulse wave signal according to the optical signal received from the light receiving sensor and analyze a magnitude, a period, and a wave change of the pulse wave signal.

23. The electronic device of claim 22, wherein the main processor is configured to identify a wave period, wherein a highest pulse wave value, a reflected pulse wave value, and a lowest pulse wave value sequentially occur in the wave period, set the period of the pulse wave signal as the wave period, and determine a pulse wave value ratio by using a ratio of the reflected pulse wave value to the highest pulse wave value (RI ratio) during the period of the pulse wave signal.

* * * * *